United States Patent
Berk et al.

(10) Patent No.: US 10,568,862 B2
(45) Date of Patent: Feb. 25, 2020

(54) XANTHONE-RICH PLANT EXTRACTS OR COMPOUNDS THEREFROM FOR MODULATING DISEASES OF THE CENTRAL NERVOUS SYSTEM AND RELATED DISORDERS

(71) Applicant: Deakin University, Waurn Ponds (AU)

(72) Inventors: Michael Berk, Waurn Ponds (AU); Wendy Laupu, Smithfield (AU)

(73) Assignee: DEAKIN UNIVERSITY, Victoria (AU)

( * ) Notice: Subject to any disclaimer, the term of this patent is extended or adjusted under 35 U.S.C. 154(b) by 0 days.

(21) Appl. No.: 15/121,652

(22) PCT Filed: Feb. 26, 2015

(86) PCT No.: PCT/AU2015/050078
§ 371 (c)(1),
(2) Date: Aug. 25, 2016

(87) PCT Pub. No.: WO2015/127512
PCT Pub. Date: Sep. 3, 2015

(65) Prior Publication Data
US 2016/0367521 A1    Dec. 22, 2016

(30) Foreign Application Priority Data
Feb. 26, 2014 (AU) .............................. 2014900627

(51) Int. Cl.
A61K 31/352 (2006.01)
A61K 36/38 (2006.01)

(52) U.S. Cl.
CPC ............ A61K 31/352 (2013.01); A61K 36/38 (2013.01)

(58) Field of Classification Search
CPC .............................. A61K 31/352; A61K 36/38
See application file for complete search history.

(56) References Cited

U.S. PATENT DOCUMENTS

| | | | |
|---|---|---|---|
| 2001/0036486 A1 | 11/2001 | Rosenthal et al. | |
| 2007/0026109 A1* | 2/2007 | Foulger | A23L 33/15 426/72 |
| 2008/0193567 A1 | 8/2008 | Barthel | |
| 2009/0062378 A1* | 3/2009 | Garrity | A23L 2/02 514/455 |
| 2013/0004533 A1 | 1/2013 | Soma et al. | |
| 2013/0034537 A1 | 2/2013 | Gocan et al. | |

FOREIGN PATENT DOCUMENTS

| | | |
|---|---|---|
| EP | 267665 A1 | 5/1988 |
| EP | 2676665 | 12/2013 |
| KR | 2014142571 | * 12/2014 |
| WO | WO-2009093255 A2 | 7/2009 |
| WO | WO-2010068815 A2 | 6/2010 |
| WO | WO-2011043735 A1 | 4/2011 |
| WO | WO-2011139778 A1 | 11/2011 |

OTHER PUBLICATIONS

Shan et al. (Curr Mol Med. Dec. 1, 2011; 11(8): 666-677).*
Bettio et al. (Pharmaceutical Biology, 49:12, 1277-1285).*
Sukma et al. (J. Ethanopharmacology 135 (2011)450-454).*
Stone (Mangosteen and mental illness,( 2009).*
Schulze et al. World J Biol Psychiatry. Apr. 2014 ; 15(3): 200-208.*
Li et al. (Planta Med 2013; 79: 646-653).*
Stone (Mangosteen and mental illness,( 2009) wayback machine.*
Jung et al. (J. Agric. Food Chem. (2006), 534, 2007-2082.*
Sahelian, R. "Mangosteen fruit supplement, benefit and side effects, research studies of juice and drink". [retrieved from internet on Mar. 23, 2015 <URL: <http://www.raysahelian.com/mangosteen.html>> published on Feb. 8, 2014 as per Wayback Machine whole document.
Wang, Y., et al., "α-Mangostin, a polyphenolic xanthone derivative from mangosteen, attenuates β-amyloid oligomers-induced neurotoxicity by inhibiting amyloid aggregation", Neuropharmacology, 2012, vol. 62, pp. 871-881 abstract.
Sukma, M., et al., "γ-Mangostin increases serotonin$_{2A/2C}$, muscarinic, histamine and bradykinin receptor mRNA expression". Journal of Ethnopharmacology, 2011, vol. 135, pp. 450-454 abstract; pp. 453-454.
Supplementary European Search Report issued in EP15755865 dated Oct. 13, 2017.
Pedraza-Chaverri, et al., Medicinal Properties of Mangosteen (*Garcinia mangostana*), Food and Chemical Toxicology, 2008, 46:3227-3239.
International Search Report issued in PCT/AU2015/050078 dated Apr. 2, 2015.

* cited by examiner

*Primary Examiner* — Shirley V Gembeh
(74) *Attorney, Agent, or Firm* — Blank Rome LLP

(57) ABSTRACT

The invention relates to a method of treatment and/or prophylaxis of a disease or disorder of the central nervous system comprising administering to a mammal in need thereof an effective amount of a xanthone-rich plant extract, or a compound derived from a xanthone-rich plant extract. The invention also relates to use of a xanthone-rich plant extract, or a compound derived from a xanthone-rich plant extract, in the preparation of a medicament for the treatment and/or prophylaxis of a disease or disorder of the central nervous system and to a xanthone-rich plant extract, or a compound derived from a xanthone-rich plant extract, for use in the treatment and/or prophylaxis of a disease or disorder of the central nervous system.

9 Claims, 14 Drawing Sheets

XANTHONE-RICH PLANT EXTRACTS OR COMPOUNDS THEREFROM FOR MODULATING DISEASES OF THE CENTRAL NERVOUS SYSTEM AND RELATED DISORDERS

This application is a national stage of International Patent Application No. PCT/AU2015/050078, filed Feb. 26, 2015, which claims the benefit of Australian Patent Application 2014900627 filed Feb. 26, 2014, each of which is hereby incorporated by reference in its entirety.

FIELD OF THE INVENTION

The present invention relates generally to a method of modulating a disease or disorder of the central nervous system in mammals and to agents for use therein. The method of the present invention is particularly useful in the treatment and/or prophylaxis neuropsychiatric or neurodegenerative conditions and related disorders in mammals, in particular, to the treatment or prophylaxis of schizophrenia.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

The details concerning the biological mechanisms underlying the development and progression of a number of diseases and disorders affecting the central nervous system including neuro-psychotic diseases, such as schizophrenia; neuro-degenerative diseases, such as Parkinson's disease; as well as addictions, such as alcohol or opiate dependency, remain unclear. Collectively, they are disabling and emotionally devastating illnesses, and options for treatment for a number of these diseases and disorders remains inadequate.

Schizophrenia, for example, is a severe mental illness which affects approximately one person in a hundred. The symptoms that are most commonly associated with the disease are called positive symptoms, that denote the presence of grossly abnormal behaviour. These include thought disorder (speech which is difficult to follow or jumping from one subject to another with no logical connection), delusions (false beliefs of persecution, guilt, grandeur or being under outside control) and hallucinations (visual or auditory). Thought disorder is the diminished ability to think clearly and logically. Often it is manifested by disconnected and nonsensical language that renders the person with schizophrenia incapable of participating in conversation, contributing to alienation from family, friends and society. Delusions are common among individuals with schizophrenia. An affected person may believe that they are being conspired against (called "paranoid delusion"). "Broadcasting" describes a type of delusion in which individuals with this illness believe that their thoughts can be heard by others. Hallucinations can be heard, seen or even felt. Most often they take the form of voices heard only by the afflicted person. Such voices may describe the person's actions, warn of danger or instruct what to do. At times the individual may hear several voices carrying on a conversation. Less obvious than the above "positive symptoms" and "thought disorder" but equally serious are the deficit or negative symptoms that represent the absence of normal behaviour. These include flat or blunted affect (i.e. lack of emotional expression), apathy, social withdrawal and lack of insight.

The onset of schizophrenia usually occurs during adolescence or early adulthood, although it has been known to develop in older people. Onset may be rapid with acute symptoms developing over several weeks, or it may be slow developing over months or even years. Schizophrenia is, in fact, a fairly common disorder. It affects both sexes equally and strikes about 1% of the population worldwide. Another 2-3% have schizotypal personality disorder, a milder form of the disease.

Like a number of other neuro-degenerative and neuro-psychotic disorders, the causes of schizophrenia are not fully understood. However, during the last few years there has emerged a body of literature which supports an abnormality in oxidation homeostasis systemically and centrally in schizophrenia. The origin of this oxidative stress is still unknown. The brain in schizophrenia exhibits many chemical hallmarks of oxidative attack, in addition to indications of altered antioxidant defence. Any tissue under sustained radical attack may suffer a depletion of the key free radical/$H_2O_2$ scavenger in the brain, glutathione. Recently, reports have emerged that glutathione is indeed depleted in schizophrenia, and that the antioxidant enzymic activities related to glutathione metabolism are markedly perturbed. Do K Q, Trabesinger A H, Kirsten-Kruger M, Lauer C J, Dydak U, Hell D, Holsboer F, Boesiger P and Cuenod M., (2000), Euro J Neurosci, 12:3721-8 have reported a significant decrease (−27%) in the cerebrospinal fluid levels of glutathione in drug-free schizophrenia patients compared to controls. This decrease is consistent with the previously reported decrease in the levels of the glutathione metabolyte gamma-glutamylglutamine in the cerebrospinal fluid of such patients (Do K Q, Lauer C J, Schreiber W, Zollinger M, Gutteck-Amsler U, Cuenod M and Holsboer F., (1995), J Neurochem, 65:2652-62). Furthermore, Do et al., (2000) also found a 52% decrease in glutathione levels in the medial prefrontal cortex of schizophrenia patients compared to controls, using a non-invasive proton magnetic resonance spectroscopy method.

Intriguingly, other aspects of the glutathione metabolic pathway are also perturbed in schizophrenia. Decreased peripheral glutathione peroxidase (GPx) activity has been described in schizophrenia patients (Abdalla D S, Monteiro H P, Oliveira J A and Bechara E J., (1986), Clin Chem, 32:805-7), and the decrease correlates with increased brain atrophy (Buckman T D, Kling A S, Eiduson S, Sutphin M S and Steinberg A., (1987), Biol Psychiatry, 22:1349-56). Plasma GPx positively correlates with psychosis rating scored in schizophrenia patients on or off medication (Yao J K, Reddy R D and van Kammen D P., (1999), Biol Psychiatry, 45:1512-5). GPx is the enzyme that catalyses the scavenging of $H_2O_2$ and other radicals by glutathione.

These biochemical changes have led to a call for the critical study of antioxidants as schizophrenia treatments utilised adjunctively with antipsychotic medication. To date, research has focused on the use of indirect means of overcoming the defects in glutathione metabolism such as increasing the efficiency of other radical scavenging systems. For example, Vitamin C, Vitamin E (alpha-tocopherol), alpha-lipoic acid supplements and also selenomethionione have been investigated. Currently, investigators are focusing on the use of Vitamins E and C (Yao et ah, 1999, supra). Selenomethionione supplementation is well known to augment the activity of glutathione peroxidase (Duffield A J, Thomson C D, Hill K E and Williams S., (1999), Am J Clin Nutr, 70:896-903). Vitamin E and selenium combined supplementation has already been reported to provide beneficial effects in the treatment of the FALS transgenic mouse model (Gurney M E, Cutting F B, Zhai P, Doble A, Taylor C P, Andrus P K and Hall E D., (1996), Ann Neurol, 39:147-57), demonstrating that the potential antioxidant benefits of such oral supplementation can also be transduced across the blood brain barrier in brain oxidation disorders. However, while being supportive of glutathione metabolism, in that these molecules can function as antioxidants, they are not the most efficient means of increasing glutathione levels in the brain.

In addition to impaired antioxidant defence, abnormalities in neurotransmitters and neuroplasticity have also been identified in patients suffering from schizophrenia (Arnold et al., 2005). Some of the implicated neurotransmitters include dopamine, GABA and acetylcholine (Zheng et al., 2012). Additionally, release of the excitatory neurotransmitter, glutamate is thought to be overstimulated in schizophrenia, leading to activation of toxic intracellular pathways involving calcium (Reiter et al., 1995). Elevations to intracellular calcium and dysfunctional calcium signalling have thus been implicated in cognitive impairment in schizophrenia (Lidow, 2003) and are known triggers for apoptosis (Mattson & Chan, 2003).

Accordingly, there is an on-going need to develop methods of treating and/or preventing schizophrenia, either in the form of adjunctive therapies to currently utilised treatments or as a replacement to the use of currently available antipsychotic medication.

Mangosteen (*Garcinia mangostana*) is an evergreen tall tree which belongs to the Clusiaceae (Guttiferae) family *Garcinia mangostana* is related to other mangosteens, such as the button mangosteen (*G. prainiana*) or the charichuelo (*G. madruno*). It originated in South East Asia, and is today cultivated as a fruit tree throughout the region, including but not limited to Thailand, India, Sri Lanka, and Malaysia. A popular eating fruit, the flesh of the mangosteen is sweet and fibrous, and is surrounded by an inedible rind, or exocarp, when ripe. In each fruit, the edible segmented flesh surrounds a seed.

The mangosteen fruit pericarp and exocarp contain a number of bioactive compounds, including, but not limited to, polyphenols, such as xanthones and tannins, as well as anthocyanins, procyanins, prodelophinidins and associated stereoisomers, such as epi-catechins. The unique composition is astringent which discourages infestation by insects, fungi, plant viruses, bacteria and animal predation. Over 85 secondary metabolites have been isolated from the pericarp of mangosteen, which includes over 60 xanthones. Xanthones have been isolated from a number of plant sources, but are particularly common to the Bonnetiaceae and Clusiaceae families and in some species in the family Podostemaceae.

As stated above, mangosteen is a popular eating fruit throughout South East Asia. Various parts of the plant have also been used in traditional medicine as an anti-inflammatory, an antimicrobial or to treat skin infections, wounds, dysentery. However, work to date on the phytochemistry of the mangosteen plant and fruit has been inconclusive and insufficient to verify its safety or efficacy for use as a supplement or for medical treatment. The applicants of the present application have now surprising found that plant extracts, such as those derived from mangosteen pericarp, and the specific compounds they contain, offer an effective adjunct or replacement therapy for the treatment and/or prophylaxis of diseases or disorders of the central nervous system, including neuro-degenerative or neuro-psychotic disorders, such as schizophrenia.

SUMMARY OF THE INVENTION

In one aspect of the invention, there is provided a method of treatment and/or prophylaxis of a disease or disorder of the central nervous system comprising administering to a mammal in need thereof an effective amount of a plant extract, or a compound derived from a plant extract.

In some embodiments, the central nervous system disease or disorder is a neurodegenerative disorder, a neuropsychiatric disorder, or a disease or disorder related to neurodegenerative or neuropsychiatric disorders. Examples of disease or disorders relevant to the present invention include schizophrenia, bipolar disorder, depression, anxiety, autism, obsessive compulsive disorder, multiple chemical sensitivity, gulf war syndrome, dementia, myalgic encephalomyelitis, chronic fatigue syndrome, acquired brain injury, multiple sclerosis, Parkinson's disease, alcohol addiction, smoking addiction, *cannabis* addiction, opiate addiction, benzodiazepine addiction, and amphetamine addiction.

In certain embodiments of the present invention, the disease or disorder is schizophrenia.

In other aspects, the method according to the present invention comprises administering an effective amount of plant extract which is a xanthone-rich plant extract. In particular, it is recognised that plant extracts from the genus Clusiaceae, Bonnetiaceae and Podostemaceae are particularly advantageous to the methods of the present invention. More particularly, the method according to the present invention comprises administering a plant extract from Clusiaceae *Garcinia mangostana* (mangosteen), especially an extract from the pericarp of the fruit of Clusiaceae *Garcinia mangostana* (mangosteen).

In further aspects, the plant extract or compound derived from a plant extract to be administered in accordance with the present invention includes a compound selected from the group consisting of xanthones, xanthenes, polyphenols, tannins, flavonoids, triterpenoids, benzophenones, biphenyl compounds, pyrroles, benzofurans, anthocyanins, procyannins, prodelphinidins, epicatechins, and combinations thereof.

In still other aspects, the plant extract or compound derived from a plant extract to be administered in accordance with the present invention includes a compound selected from the group consisting of:

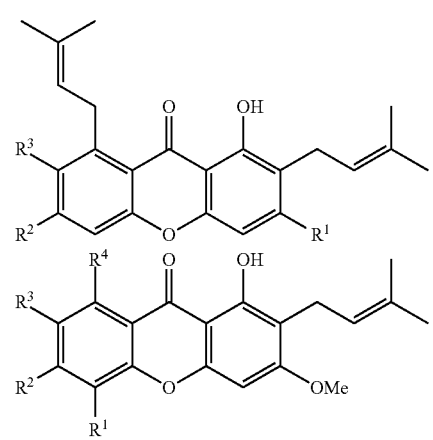

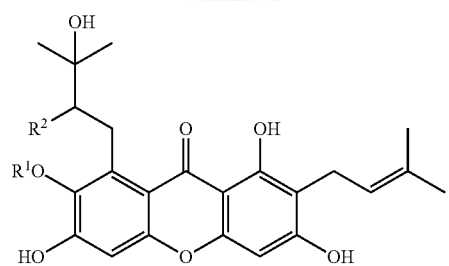
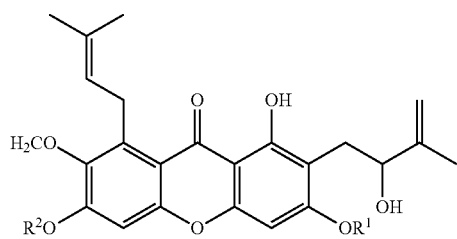
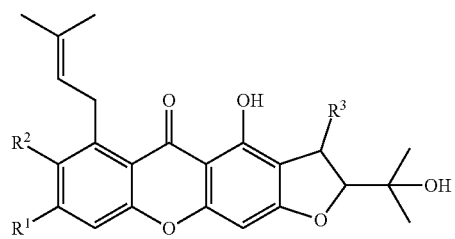
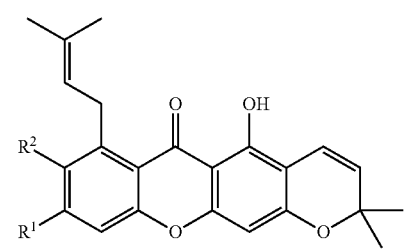
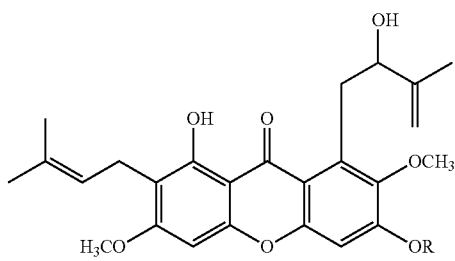
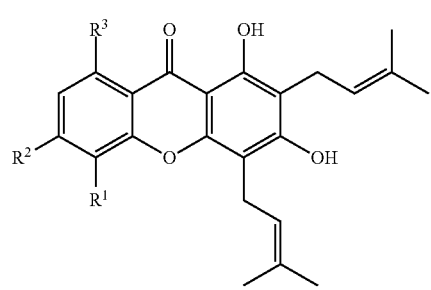
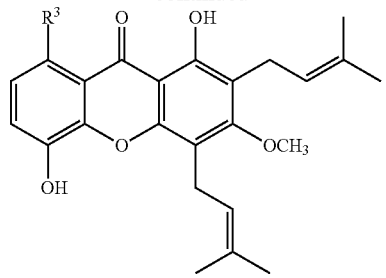
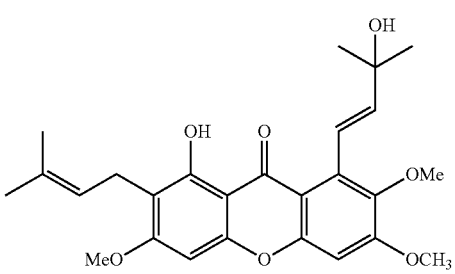
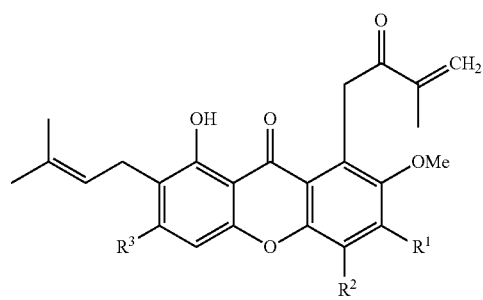
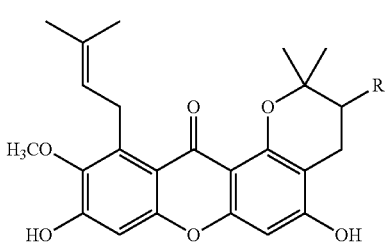
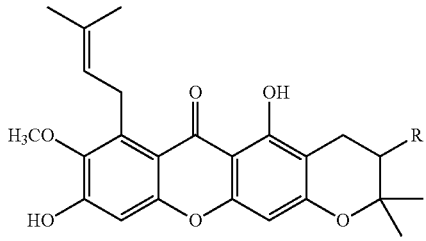
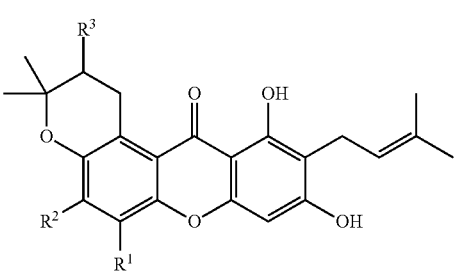

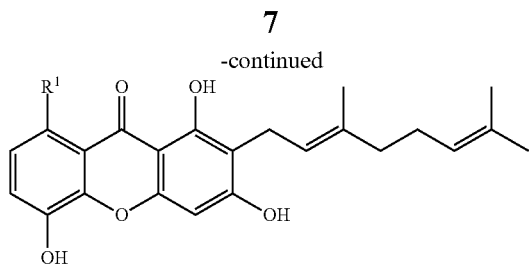
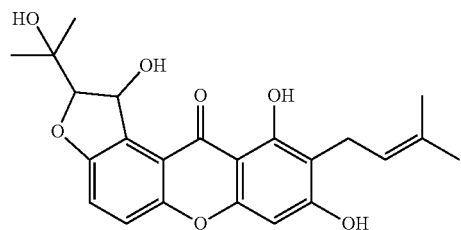
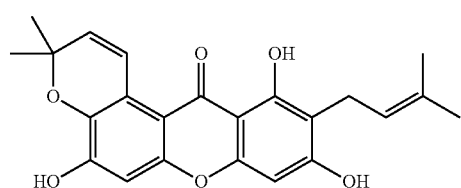
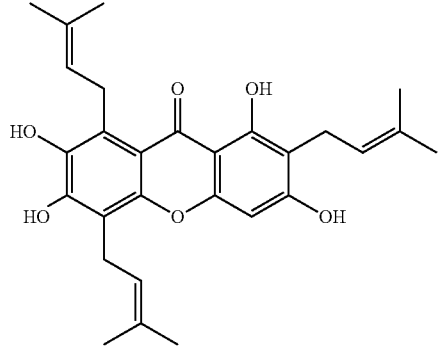
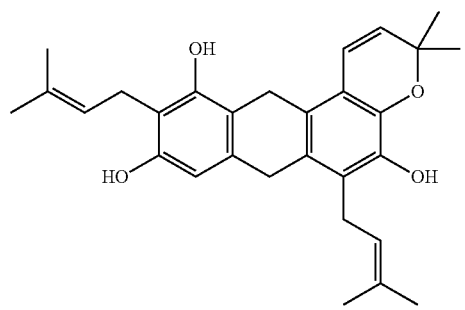
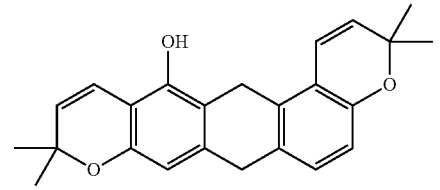
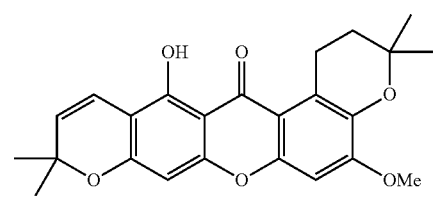
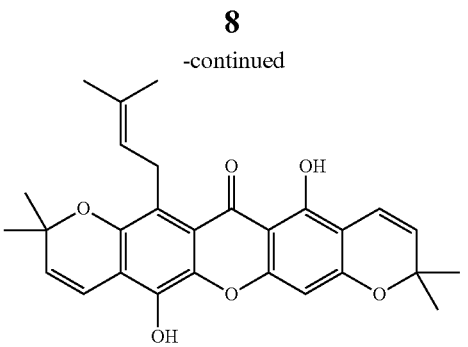
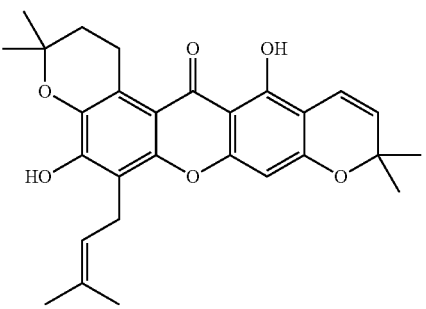
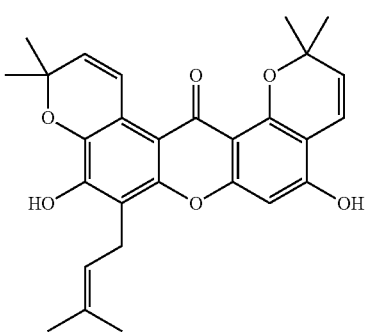
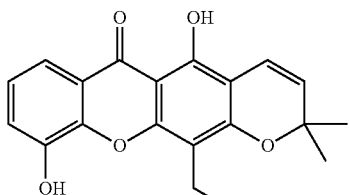
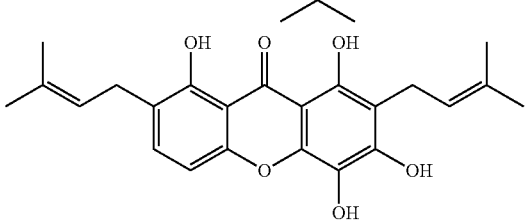
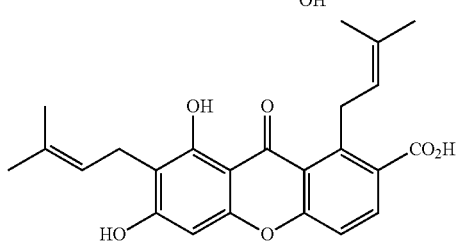

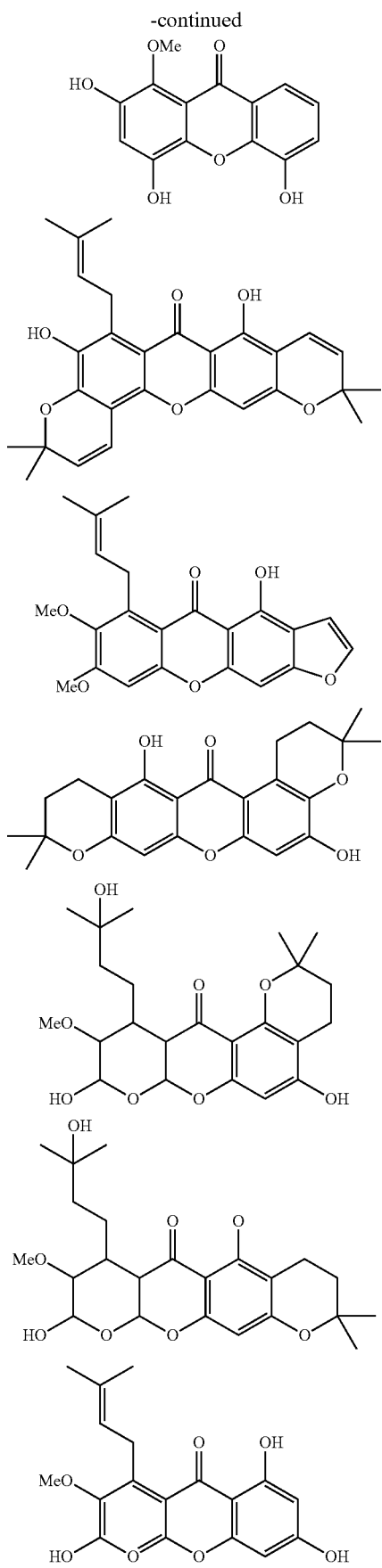
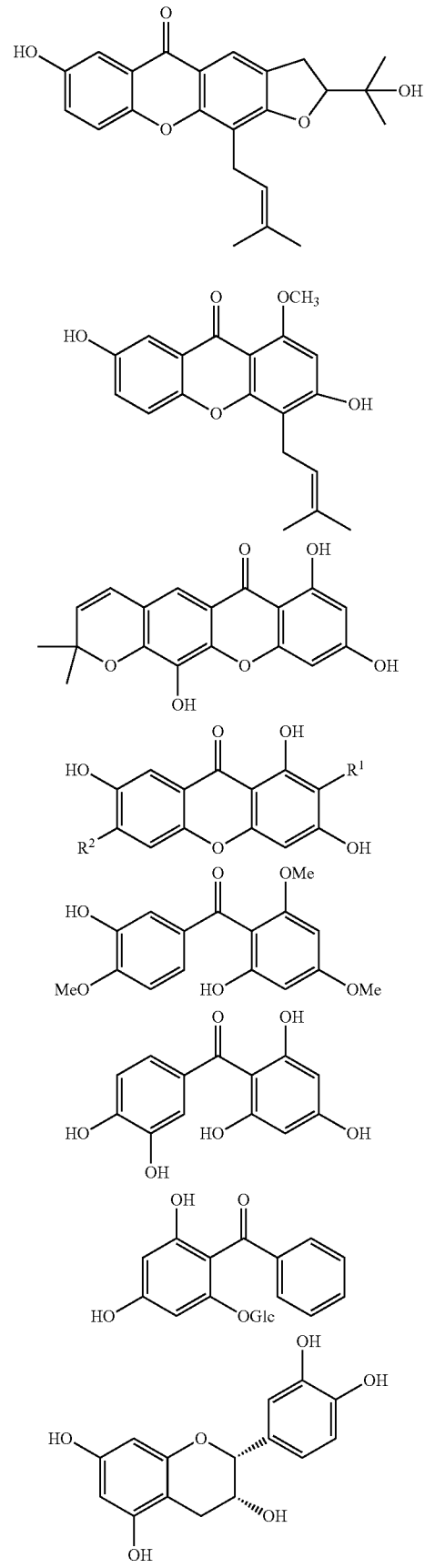

-continued
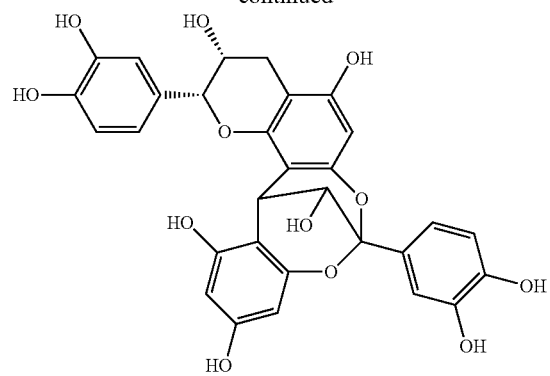
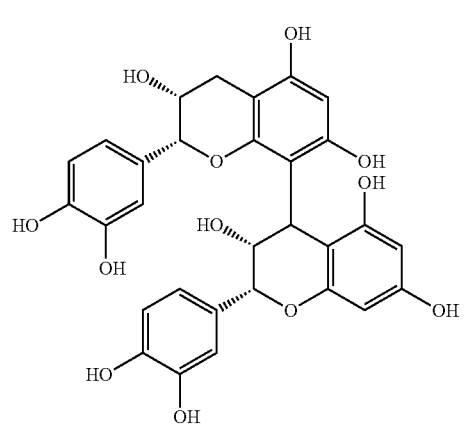
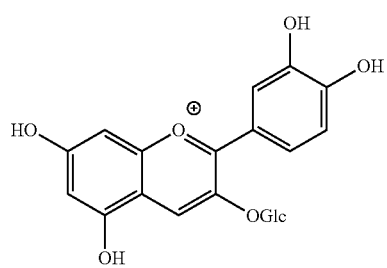
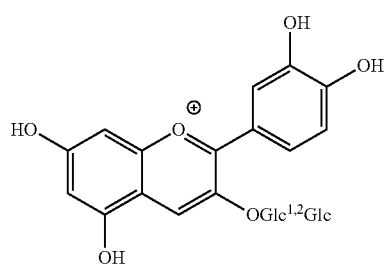
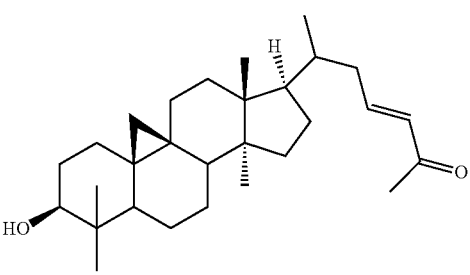
-continued
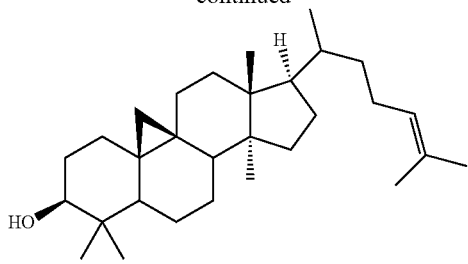
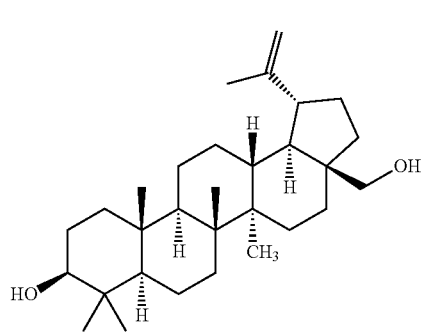
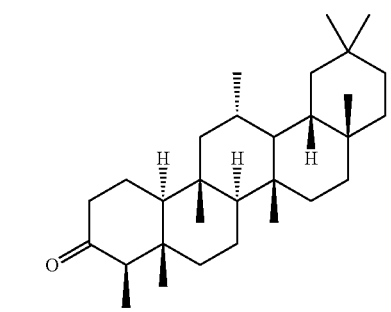
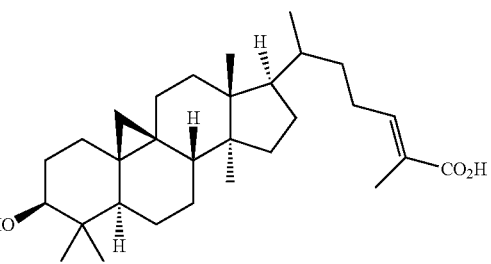
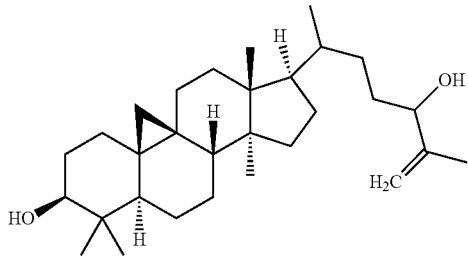
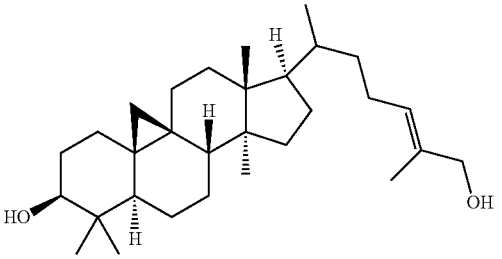

-continued

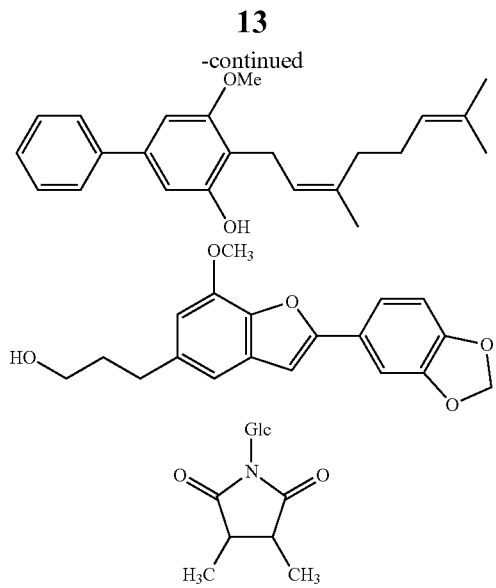

pharmaceutically acceptable salts, hydrates, and combinations thereof.

In particular, the plant extract or compound derived from a plant extract of the present invention includes a compound selected from the group consisting of:

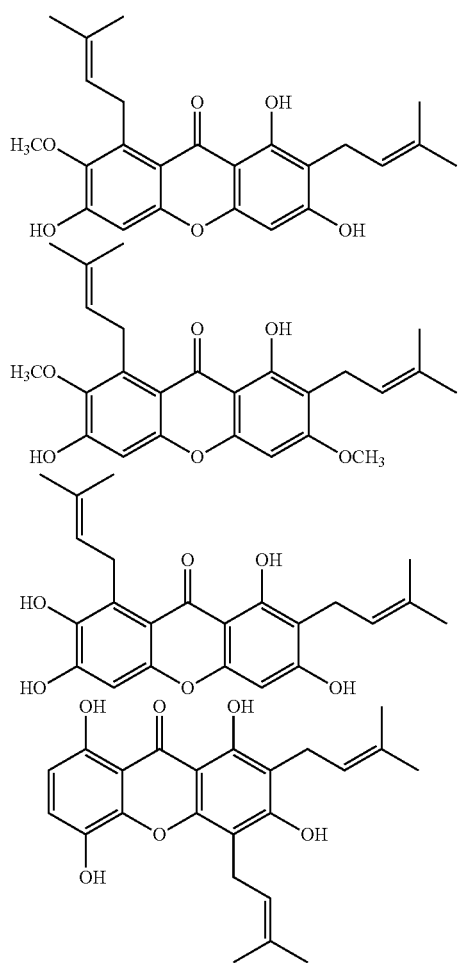

-continued

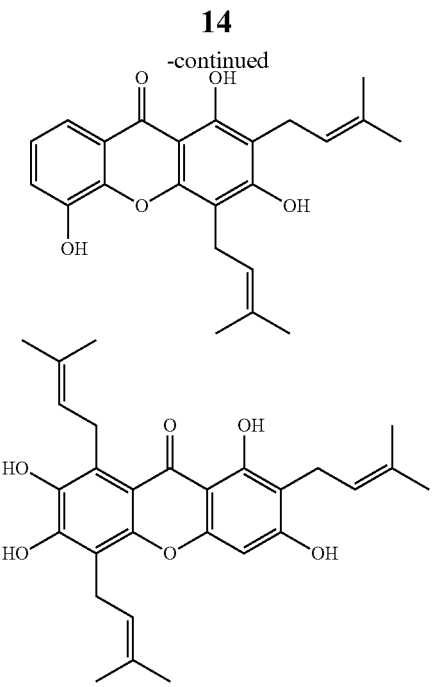

pharmaceutically acceptable salts, hydrates, and combinations thereof. More particularly, the plant extract or compound derived from a plant extract comprises:

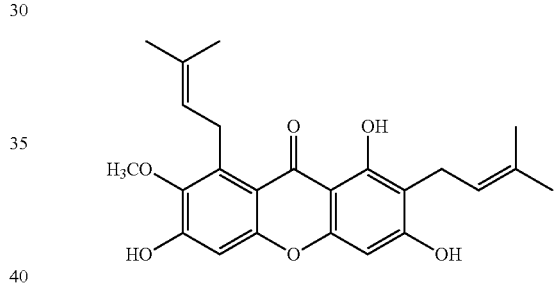

pharmaceutically acceptable salts and hydrates thereof.

In still other aspects, the present invention provides the use of a plant extract or compound derived from a plant extract, in the preparation of a medicament for the treatment and/or prophylaxis of a disease or disorder of the central nervous system.

In still further aspects, the present invention provides a plant extract, or a compound derived from a plant extract, for use in the treatment and/or prophylaxis of a disease or disorder of the central nervous system.

In particular aspects of the present invention, the plant extract or compound derived from a plant extract for use in accordance with the present invention comprises one or more compounds selected from the group consisting of xanthones, xanthenes, polyphenols, tannins, flavonoids, triterpenoids, benzophenones, biphenyl compounds, pyrroles, benzofurans, anthocyanins, procyannins, prodelphinidins, epicatechins, and combinations thereof.

Unless otherwise defined, all technical and scientific terms used herein have the same meaning as commonly understood by one of ordinary skill in the art to which this invention belongs.

DETAILED DESCRIPTION OF THE INVENTION

Figure 1:
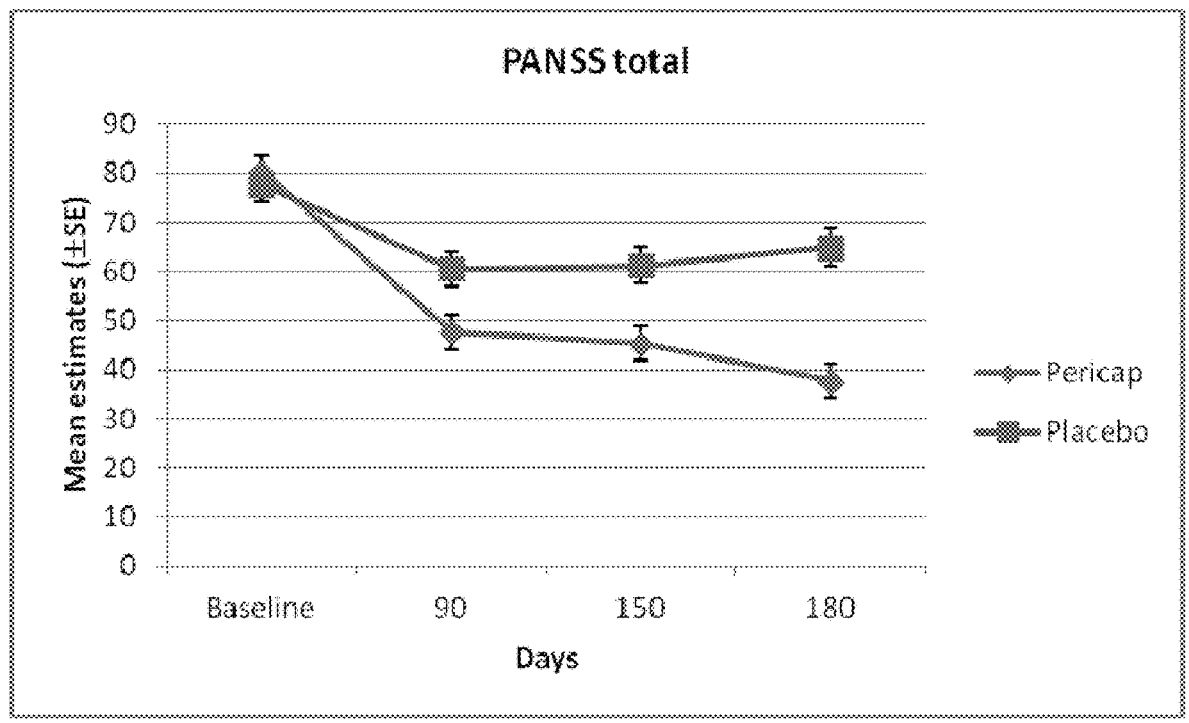
FIG. 1: Positive and Negative Syndrome Scale (PANSS) for total symptoms of schizophrenia as a measure of primary outcome for full patient cohort, measured at time points baseline (0 months), 3 months, 5 months, 6 months; PANSS total was measured across 30 items on a scale of 1-7. The lowest score was 30 (normal) and the highest possible score was 210.
Figure 2:
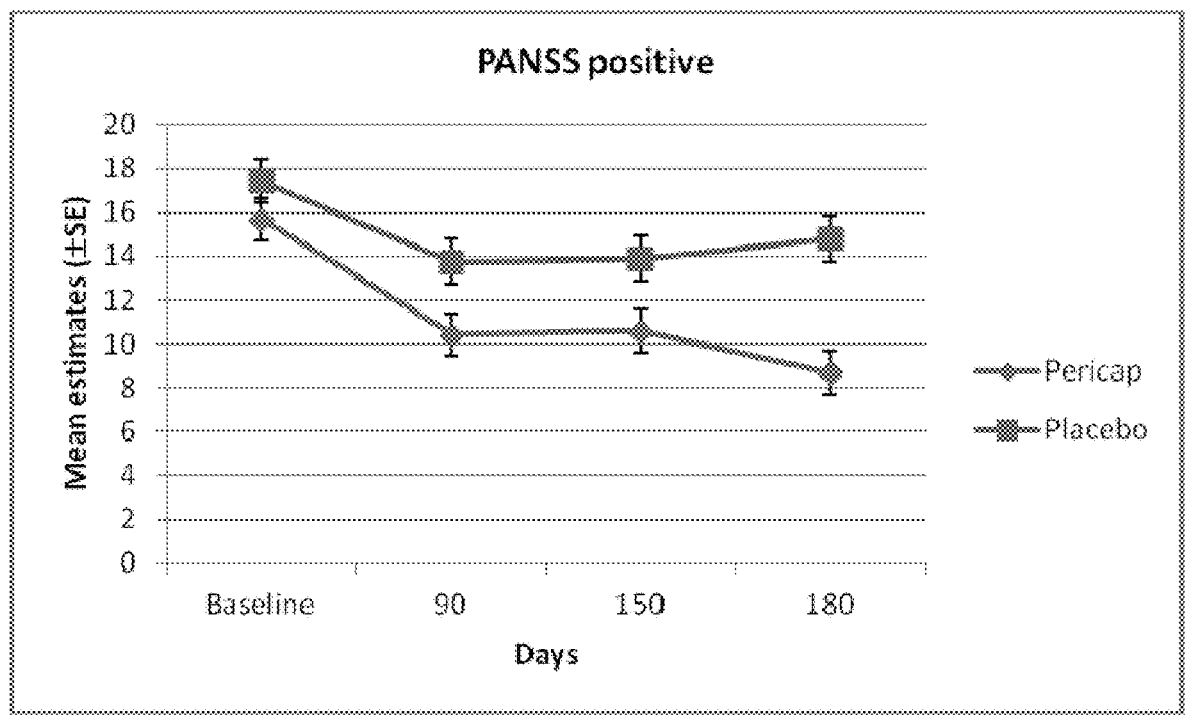
FIGS. 2 and 3: Full patient cohort data for Positive and Negative Symptom Scale (PANSS), measured at time points baseline (0 months), 3 months, 5 months, 6 months; PANSS for positive and negative symptoms of schizophrenia was measured across 7 items on a scale of 1 to 7. The lowest score was 0 and the highest possible score was 49.
Figure 3:
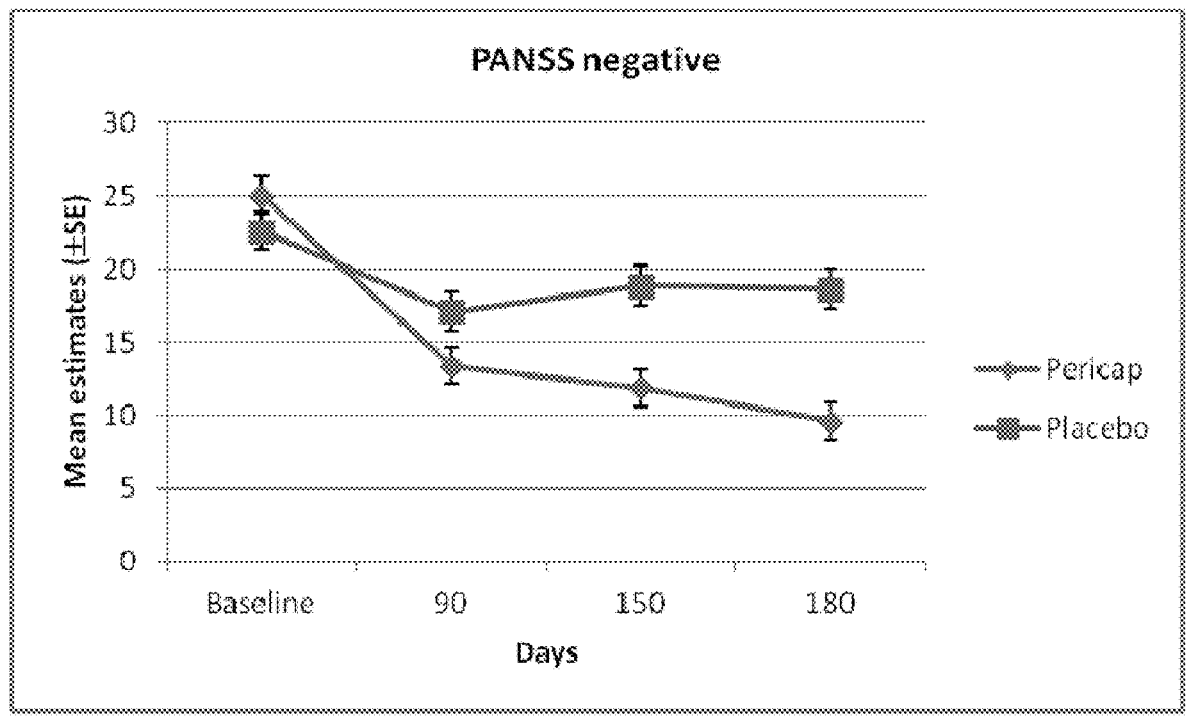
Figure 4:
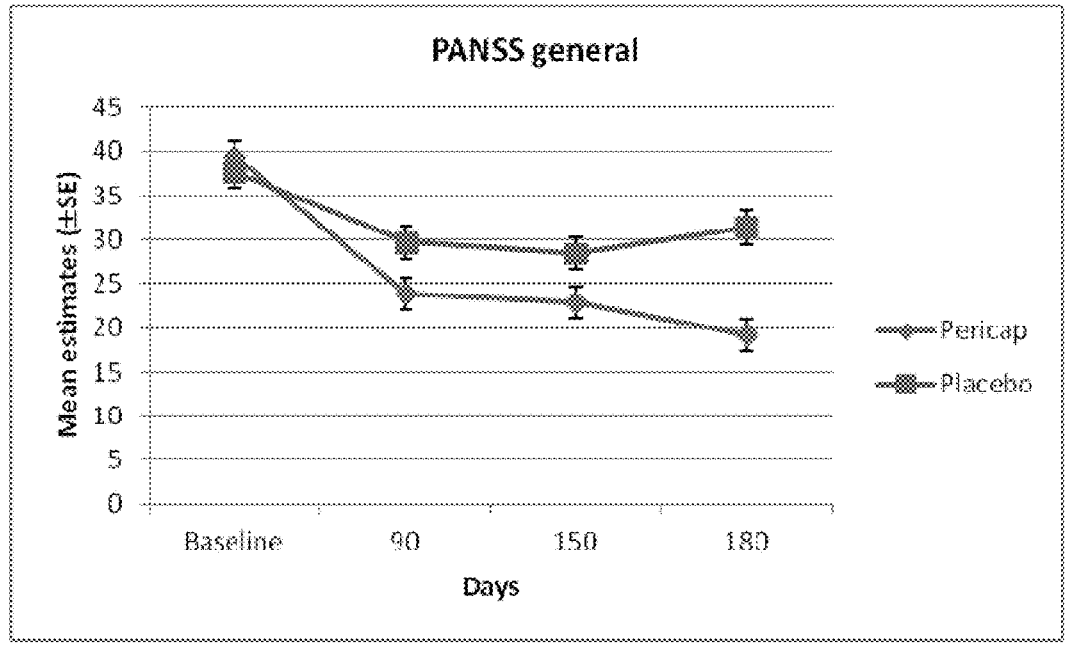
FIG. 4: Full patient cohort data for Positive and Negative Symptom Scale (PANSS) for general symptoms, measured at time points baseline (0 months), 3 months, 5 months, 6 months; PANSS for general symptoms of schizophrenia is measured across 16 items on a scale of 1 to 7. The lowest score was 16 and the highest possible score was 112.
Figure 5:
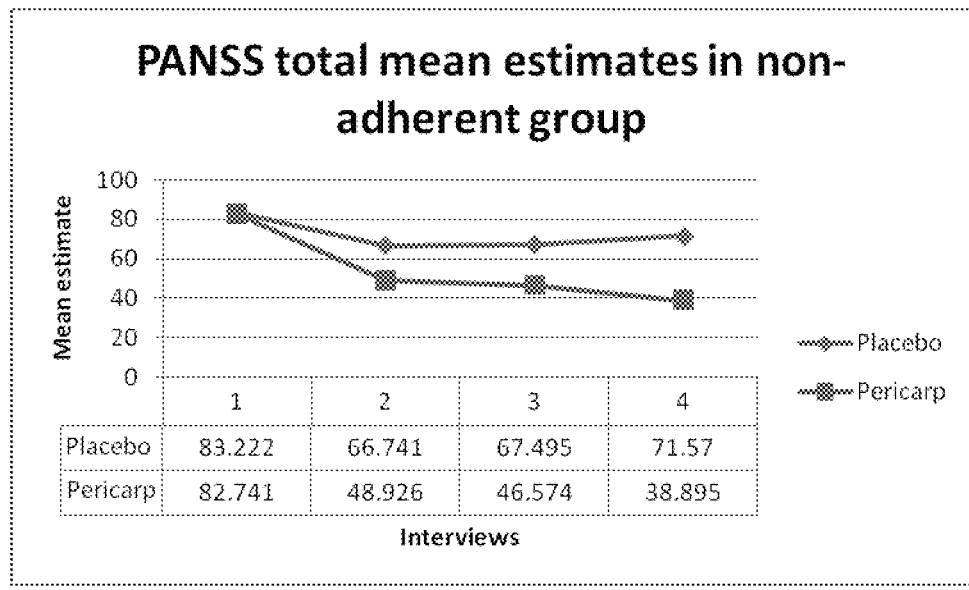
FIG. 5: Positive and Negative Syndrome Scale (PANSS) for total symptoms of schizophrenia as a measure of primary outcome for patient cohort who acknowledged poor or non-adherence to standard prescribed medication, measured at time points baseline (0 months), 3 months, 5 months, 6 months; PANSS total was measured across 30 items on a scale of 1-7. The lowest score was 30 (normal) and the highest possible score was 210.
Figure 6:
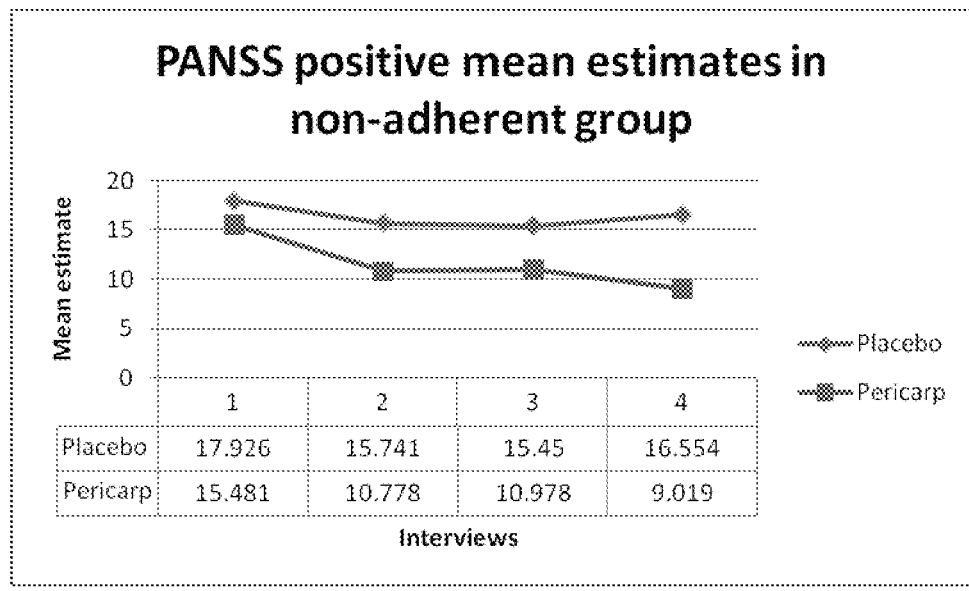
FIGS. 6 and 7: Positive and Negative Symptom Scale (PANS S) for patient cohort who acknowledged poor or non-adherence to standard prescribed medication, measured at time points baseline (0 months), 3 months, 5 months, 6 months; PANSS for positive and negative symptoms of schizophrenia was measured across 7 items on a scale of 1 to 7. The lowest score was 0 and the highest possible score was 49.
Figure 7:
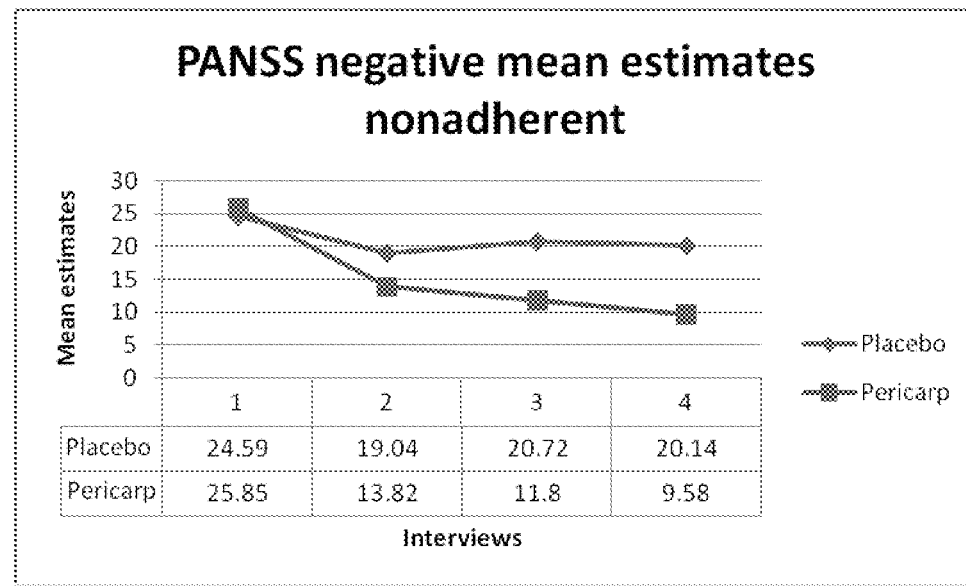
Figure 8:
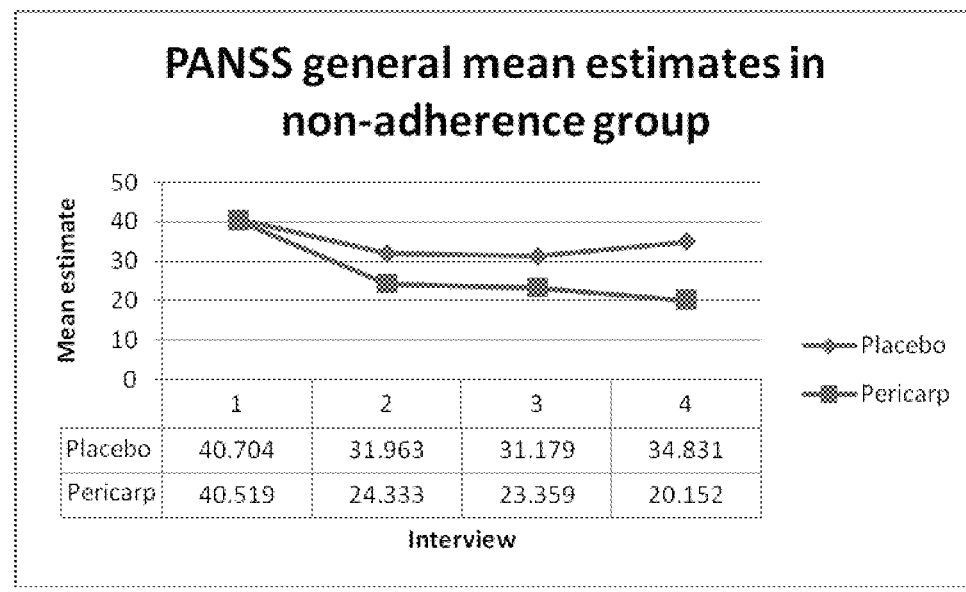
FIG. 8: Positive and Negative Symptom Scale (PANSS) for general symptoms for patient cohort who acknowledged poor or non-adherence to standard prescribed medication, measured at time points baseline (0 months), 3 months, 5 months, 6 months; PANS S for general symptoms of schizophrenia was measured across 16 items on a scale of 1 to 7. The lowest score was 16 and the highest possible score was 112.

The present invention relates to methods of treating diseases or disorders of the central nervous system with plant extracts and/or their compounds isolated or derived from a plant extract. In particularly, the present invention relates to the use of xanthone-rich plant extracts, and their compounds isolated or derived from a plant extract, such as extracts from Bonnetiaceae, Clusiaceae or Podostemaceae. More particularly, the present invention relates to methods of treating diseases or disorders of the central nervous system with extracts from *Garcinia mangostana*, (mangosteen) especially extracts from mangosteen pericarp.

Accordingly, one aspect of the present invention is directed to a method of treatment and/or prophylaxis of a disease or disorder of the central nervous system comprising administering to a mammal in need thereof an effective amount of a plant extract, or a compound derived from a plant extract.

In particular, the method of the present invention advantageously provides a method of treatment and/or prophylaxis central nervous system diseases or disorders such as neurodegenerative disorder, a neuropsychiatric disorder, or a disease or disorder related to neurodegenerative or neuropsychiatric disorders. Examples of disease or disorders relevant to the present invention include schizophrenia, bipolar disorder, depression, anxiety, autism, obsessive compulsive disorder, multiple chemical sensitivity, gulf war syndrome, dementia, myalgic encephalomyelitis, chronic fatigue syndrome, acquired brain injury, multiple sclerosis, Parkinson's disease, alcohol addiction, smoking addiction, *cannabis* addiction, opiate addiction, benzodiazepine addiction, and amphetamine addiction. In certain aspects, the methods of the present invention are particularly effective for the treatment and/or prophylaxis of a condition which is characterised by one or more symptoms of schizophrenia.

In other aspects, the method according to the present invention comprises administering an effective amount of plant extract which is a xanthone-rich plant extract. In particular, it is recognised that plant extracts from the genus Clusiaceae, Bonnetiaceae and Podostemaceae are particularly advantageous to the methods of the present invention. More particularly, the method according to the present invention comprises administering a plant extract from Clusiaceae *Garcinia mangostana* (mangosteen), especially an extract from the pericarp of the fruit of Clusiaceae *Garcinia mangostana* (mangosteen).

The methods of the present invention advantageously provide a reduction of core symptom domains in neurodegenerative disorder, a neuropsychiatric disorder, or a disease or disorder related to neurodegenerative or neuropsychiatric disorders. In some aspects, the methods of the present invention advantageously provide a reduction in the severity and frequency of symptoms of schizophrenia, for example, suicidal ideation.

Preferably the person is in need of such treatment, although the compound may be administered in a prophylactic sense.

References to a "neuro-psychiatric condition", a "neuro-psychiatric disorder" or a "neuro-psychiatric diseases", are used interchangeably, and should be understood as a reference to a condition characterised by neurologically based cognitive, emotional and behavioural disturbances. Examples of such conditions include, inter alia, a condition characterised by one or more symptoms of schizophrenia, schizotypal personality disorder, psychosis, bipolar disorder, manic depression, affective disorder, or schizophreniform or schizoaffective disorders, psychotic depression, anxiety, autism, drug induced psychosis, delirium, alcohol withdrawal syndrome, dementia induced psychosis, clinical depression, obsessive compulsive disorder, multiple chemical sensitivity, gulf war syndrome, dementia, and chronic fatigue syndrome.

In one embodiment, said neuropsychiatric condition is a condition which is characterised by one or more symptoms of schizophrenia.

Reference to "symptoms characteristic of schizophrenia" should be understood as a reference to any one or more symptoms which may occur in an individual suffering from schizophrenia. These symptoms may be evident throughout the disease course or they may be evident only transiently or periodically. For example, the hallucinations associated with schizophrenia usually occur in periodic episodes while the characteristic social withdrawal may exhibit an ongoing manifestation. It should also be understood that the subject symptoms may not necessarily be exhibited by all individuals suffering from schizophrenia. For example, some individuals may suffer from auditory hallucinations only while others may suffer only from visual hallucinations. However, for the purpose of the present invention, any such symptoms, irrespective of how many or few schizophrenia patients ever actually exhibit the given symptom, are encompassed by this definition. Without limiting the present invention to any one theory or mode of action, the symptoms that are most commonly associated with the disease are called positive symptoms (which denote the presence of grossly abnormal behaviour), thought disorder and negative symptoms. Thought disorder and positive symptoms include speech which is difficult to follow or jumping from one subject to another with no logical connection, delusions (false beliefs of persecution, guilt, grandeur or being under outside control) and hallucinations (visual or auditory). Thought disorder is the diminished ability to think clearly and logically. Often it is manifested by disconnected and nonsensical language that renders the person with schizophrenia incapable of participating in conversation, contributing to alienation from family, friends and society. Delusions are common among individuals with schizophrenia. An affected person may believe that they are being conspired against (called "paranoid delusion"). "Broadcasting" describes a type of delusion in which the individual with this illness believes that their thoughts can be heard by others. Hallucinations can be heard, seen or even felt. Most often they take the form of voices heard only by the afflicted person. Such voices may describe the person's actions, warn of danger or tell him what to do. At times the individual may hear several voices carrying on a conversation. Less obvious than the "positive symptoms" but equally serious are the deficit or negative symptoms that represent the absence of normal behaviour. These include flat or blunted affect (i.e. lack of emotional expression), apathy, social withdrawal and lack of insight. Both the positive symptoms and the negative symptoms should be understood to fall within the definition of "symptoms characteristic of schizophrenia".

In addition to the fact that there may be significant variation between schizophrenia patients in terms of which symptoms they exhibit, it should also be understood that there are other neuropsychiatric conditions which are also characterised by one or more of these symptoms. Hallucinations, for example, are also commonly observed in patients with bipolar disorder, psychotic depression, delirium and dementia induced psychosis, for example. Accordingly, reference to a condition characterised by one or more symptoms characteristic of schizophrenia should be understood as a reference to any neuropsychiatric condition which is characterised by the presence of one or more of these symptoms. In one embodiment, said condition is schizophrenia.

In one embodiment, said condition is a condition characterised by one or more symptoms of schizophrenia.

In another embodiment, said condition is schizophrenia.

In some embodiments, the present invention provides a method of treatment or prophylaxis of a neurodegenerative condition. References to a "neurodegenerative condition", a "neurodegenerative disorder" or a "neurodegenerative disease", are used interchangeably, and should be understood as a reference to a condition characterised progressive loss of structure or function of neurons, including death of neurons. Such conditions include, but are not limited to, multiple sclerosis, conditions of the central or peripheral nervous system or systemic organ associated with a disorder in protein folding or aggregation, or amyloid formation, deposition, accumulation, or persistence; abnormal protein folding, abnormal protein aggregation, amyloid formation, deposition, accumulation, or persistence, or amyloid lipid interactions conditions causing the dissociation of abnormally aggregated proteins and/or dissolving or disrupting pre-formed or pre-deposited amyloid fibril or amyloid in a subject; conditions of the central or peripheral nervous system or systemic organ resulting in the deposition of proteins, protein fragments and peptides in beta-pleated sheats and/or fibrils and/or aggregates; amyloid angiopathy; mild cognitive impairment; Alzheimer's disease-related dementia; tauopathy; alpha-synucleinopathy; Amyotrophic Lateral Sclerosis; motor neuron disease; spastic paraplegia; Huntington's Disease, spinocerebellar ataxia, Freidrich's Ataxia; neuro degenerative diseases associated with intracellular and/or intraneuronal aggregates of proteins with polyglutamine, polyalanine or other repeats arising from pathological expansions of tri- or tetra-nucleotide elements within corresponding genes; cerebrovascular diseases; Down's syndrome; head trauma with post-traumatic accumulation of amyloid beta peptide; Prion related disease; Familial British Dementia; Familial Danish Dementia; Presenile Dementia with Spastic Ataxia; Cerebral Amyloid Angiopathy, British Type; Presenile Dementia With Spastic Ataxia Cerebral Amyloid Angiopathy, Danish Type; Familial encephalopathy with neuroserpin inclusion bodies (FENIB); Amyloid Polyneuropathy; Inclusion Body myositis due to amyloid beta peptide; Familial and Finnish Type Amyloidosis; Systemic amyloidosis associated with multiple myeloma; Familial Mediterranean Fever; chronic infections and inflammations; and Type II Diabetes Mellitus associate with islet amyloid polypeptide (IAPP); vascular caused Alzheimer's Disease, Alzheimer dementia and tauopathy selected from the group of argyrophilic grain dementia, corticobasal degeneration, dementia pugilistica, diffuse neurofibrillary tangles with calcification, frontotemporal dementia with parkinsonism, Prion-related disease, Hallervorden-Spatz disease, myotonic dystrophy, Niemann-Pick disease type C, non-Guamanian Motor Neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, tangle only dementia; alpha-synucleinopathy selected from the group of dementia with Lewy bodies, multiple system atrophy with glial cytoplasmic inclusions, Shy-Drager syndrome, striatonigral degeneration, olivopontocerebellar atrophy, neurodegeneration with brain iron accumulation type I, olfactory dysfunction, and amyotrophic lateral sclerosis; motor neuron disease is associated with filaments and aggregates of neurofilament and/or superoxide dismutase proteins, spastic paraplegia associated with defective function of chaperones and/or triple A proteins and the spinocerebellar ataxia is DRPLA or Machado-Joseph Disease; Prion related disease selected from the group of Creutzfeldt-Jakob disease, Gerstmann-Straussler-Scheinker disease, and variant Creutzfeldt-Jakob disease, as well as amyloid polyneuropathy including senile amyloid polyneuropathy or systemic amyloidosis.

In still other embodiments, the present invention provides a method of treating, or preventing addiction, or the symptoms associated with addiction, including but not limited to alcohol, smoking, *cannabis*, opiate, benzodiazepine, amphetamine and related compound addictions.

The term "mammal" as used herein includes humans, primates, livestock animals (e.g. horses, cattle, sheep, pigs, donkeys), laboratory test animals (e.g. mice, rats, guinea pigs), companion animals (e.g. dogs, cats) and captive wild animals (e.g. kangaroos, deer, foxes). Preferably, the mammal is a human.

Plant extracts are recognised as rich sources of bioactive compounds. In some aspects, the methods of the present invention provide methods of treatment or prophylaxis comprising administering a plant extracts. In some embodiments, the methods of the present invention comprise administering a xanthone-rich plant extract. In some embodiments, the xanthone-rich extract is an extract derived from plant material or components from the genus Bonnetiaceae, Clusiaceae or Podostemaceae. In still other embodiments, the extract of the present invention is an extract isolated, sourced or derived from plant material or components from *Garcinia mangostana*, also referred to as mangosteen. In further embodiments, the extract of the present invention is an extract derived from the fruit of *Garcinia mangostana*; in particular from the pericarp of the fruit, that is mangosteen pericarp.

In still other aspects, the methods of the present invention provide methods of treatment or prophylaxis comprising administering one or more compounds which are isolated, sourced or derived from a plant extract. In some embodiments, the one or more compounds which are isolated, sourced or derived from a plant extract are from the genus Bonnetiaceae, Clusiaceae or Podostemaceae. In still other embodiments, the one or more compounds isolated, sourced or derived from a plant extract are from *Garcinia mangostana*, also referred to as mangosteen. In further embodiments, one or more compounds isolated, sourced or derived from a plant extract are from the fruit of *Garcinia mangostana*; in particular from the pericarp of the fruit, that is mangosteen pericarp.

The pericarp of mangosteen has been found to comprise a number of bioactive compounds. Some of the bioactive compounds found in mangosteen pericarp include xanthones, xanthenes, polyphenols, tannins, flavonoids, triterpenoids, benzophenones, biphenyl compounds, pyrroles, benzofurans, anthocyanins, procyannins, prodelphinidins, epicatechins, derivatives and isomers thereof. The bioactivity of these compounds are particularly advantageous to the methods of the present invention.

Accordingly, in some embodiments the present invention provides methods of treatment or prophylaxis comprising administering a plant extract which includes a compound selected from the group consisting of xanthones, xanthenes, xanthonoids, polyphenols, tannins, flavonoids, triterpenoids, benzophenones, biphenyl compounds, pyrroles, benzofurans, anthocyanins, procyannins, prodelphinidins, epicatechins, and combinations thereof. In particular embodiments, the methods described herein provide administration of a plant extract which includes one or more xanthone.

In other embodiments, the present invention provides methods of treatment or prophylaxis comprising administering a compound which is isolated or sourced from a plant extract selected from the group consisting of xanthones, xanthenes, xanthonoids, polyphenols, tannins, flavonoids, triterpenoids, benzophenones, biphenyl compounds, pyrroles, benzofurans, anthocyanins, procyannins, prodelphinidins, epicatechins and combinations thereof. In particular embodiments, the methods described herein provide administration of one or more xanthone.

In other embodiments, the present invention provides methods of treatment or prophylaxis comprising administering a plant extract which includes a compound selected from the group consisting of:

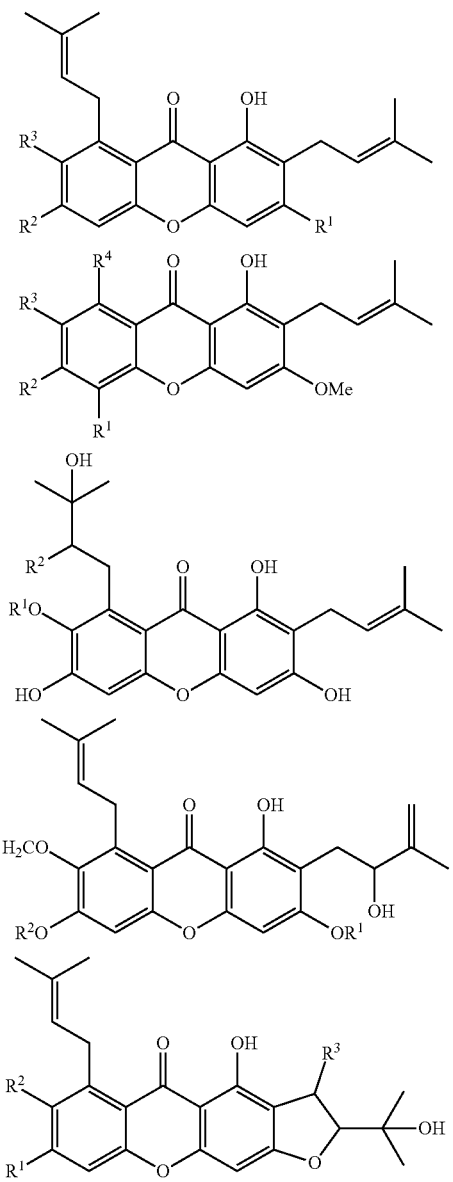

-continued

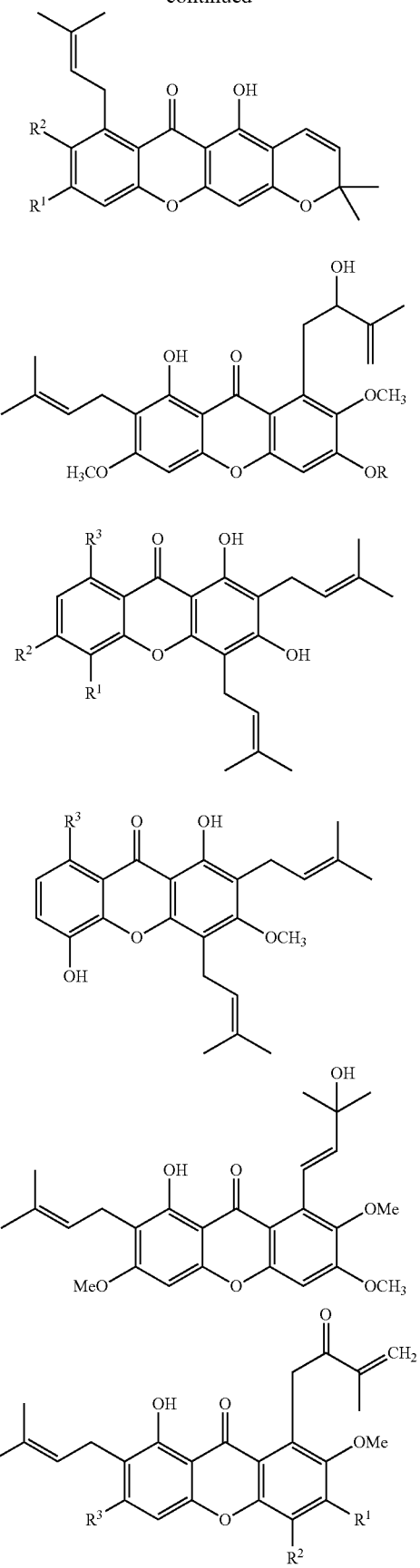

-continued
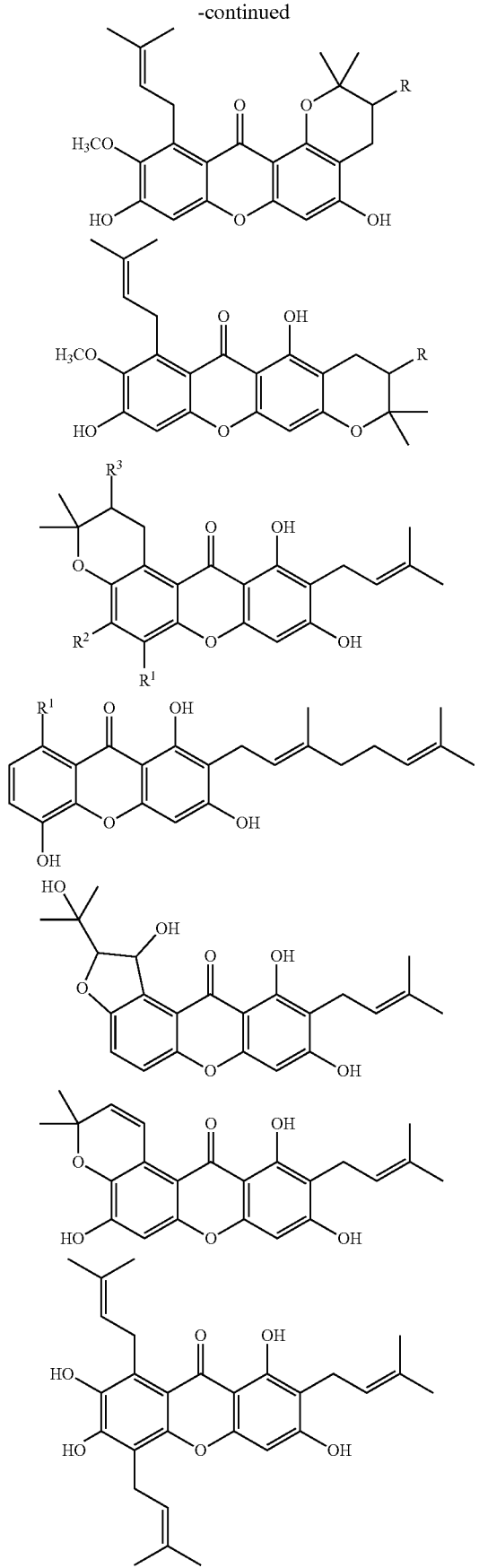
-continued
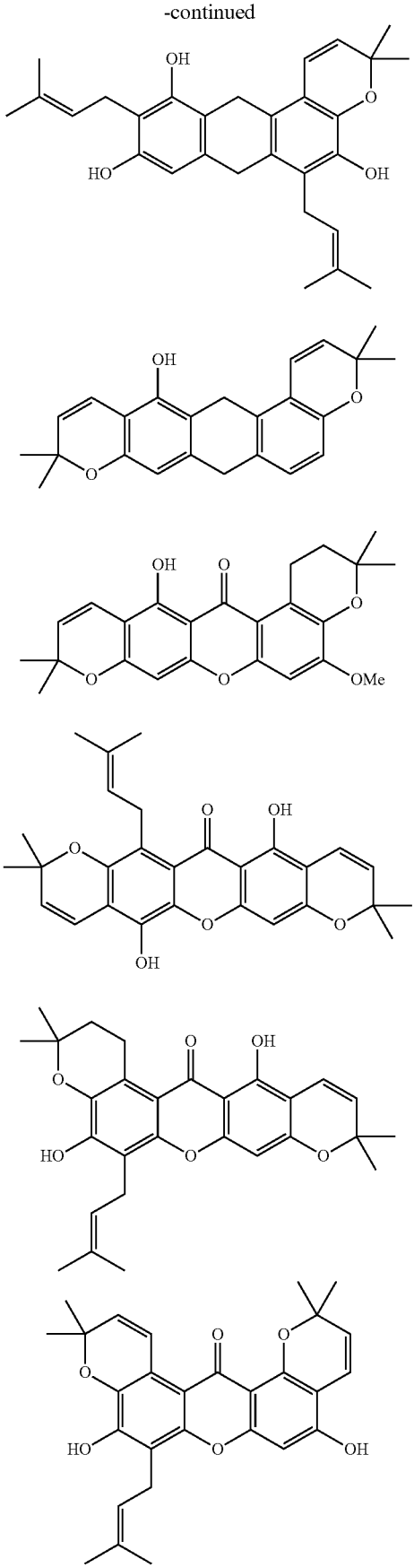

-continued
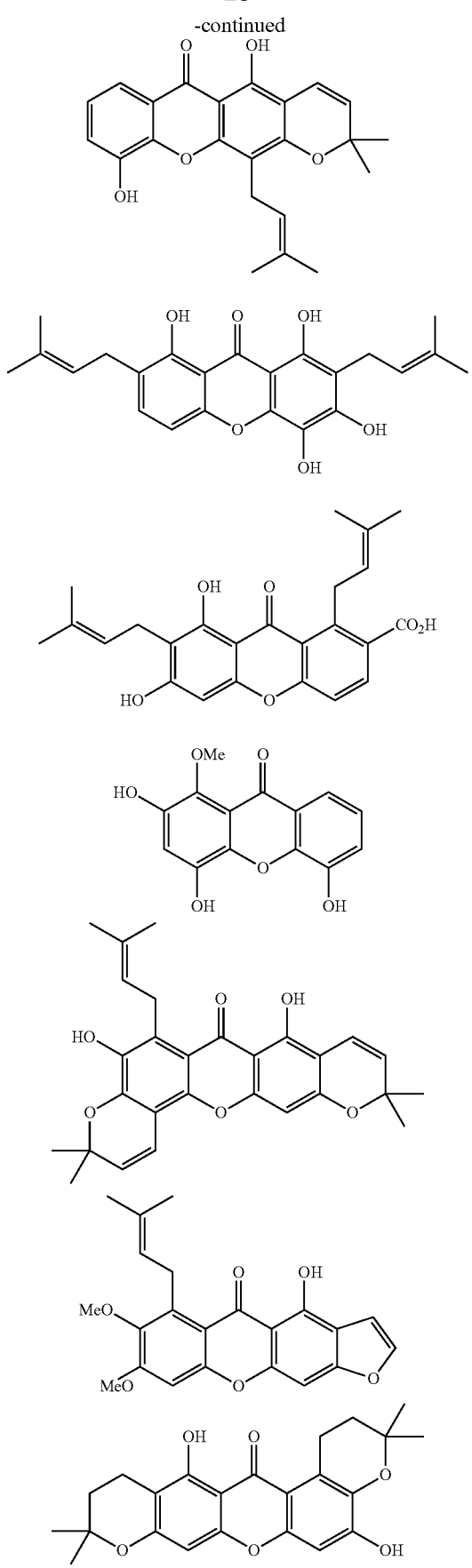
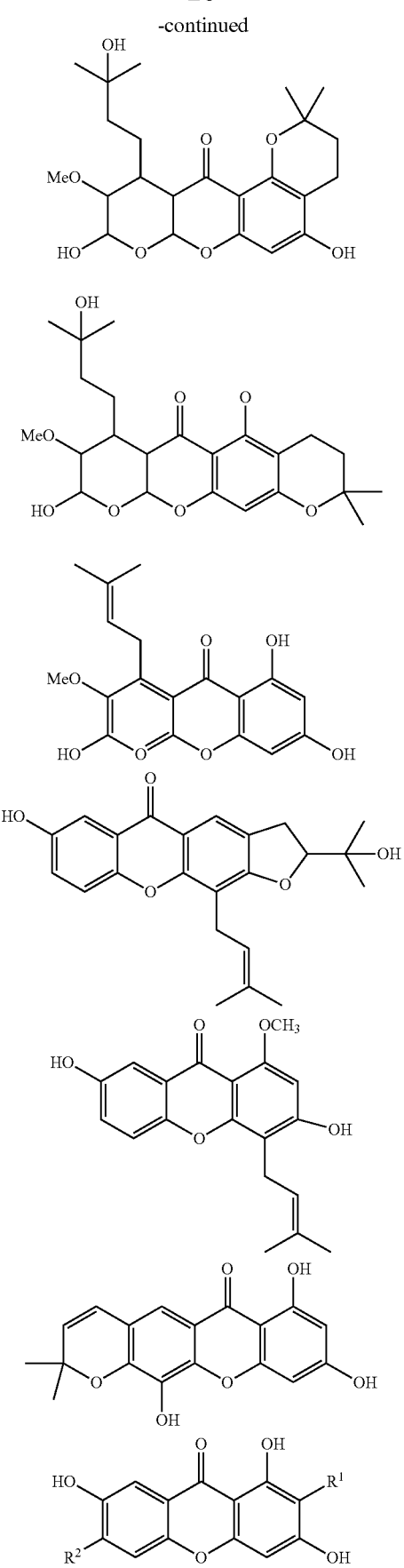

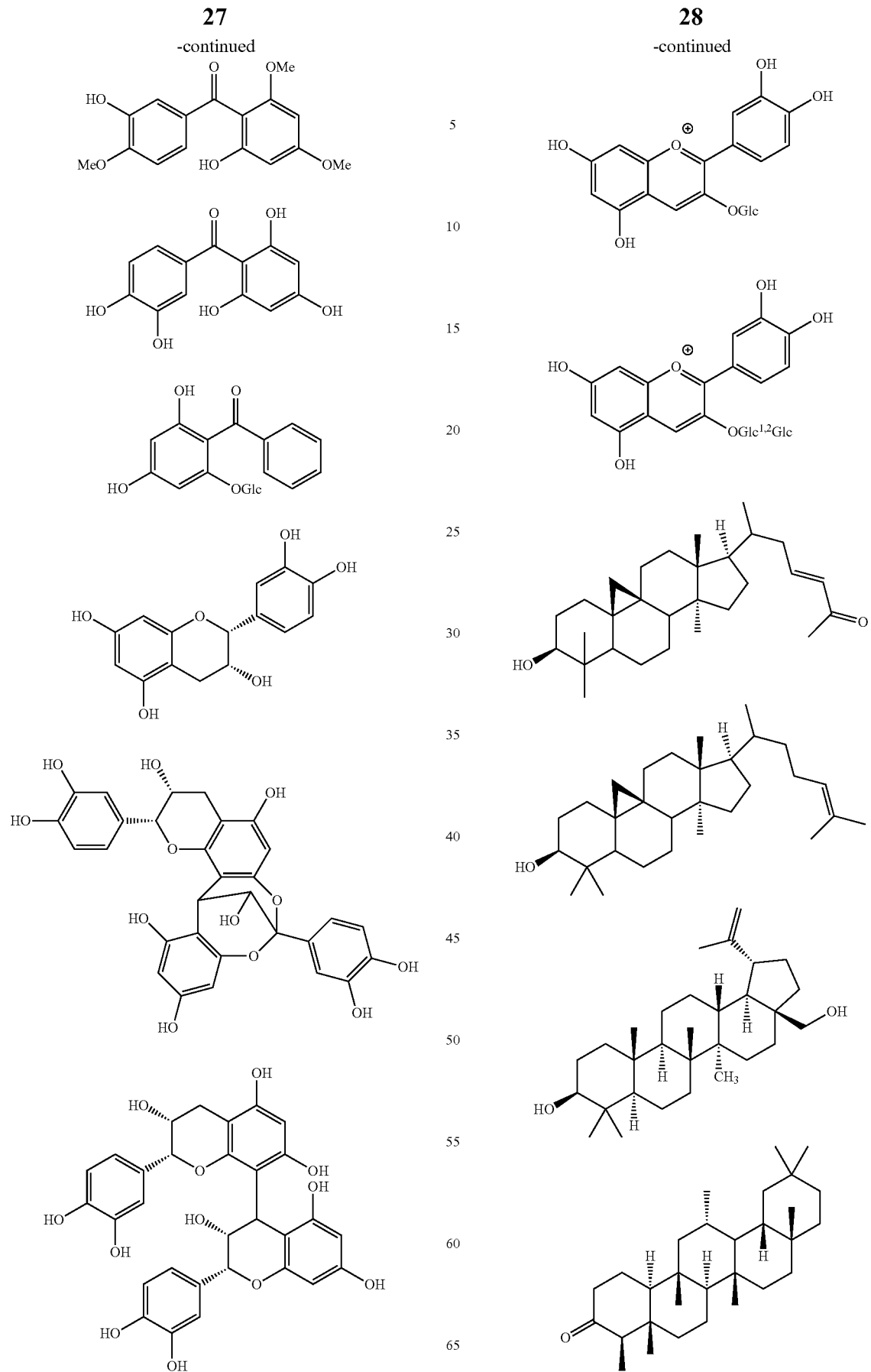

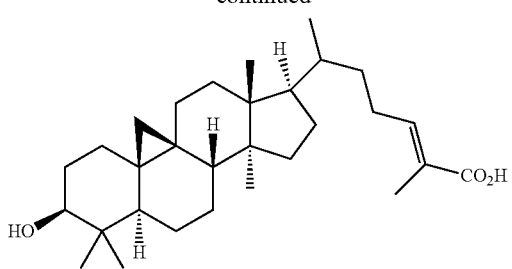
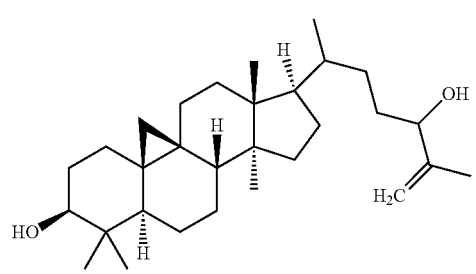
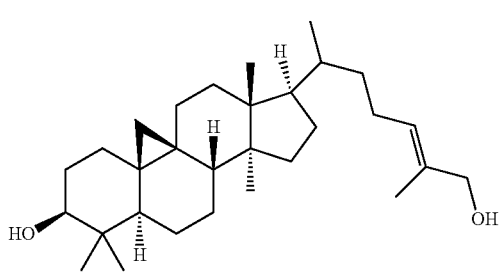
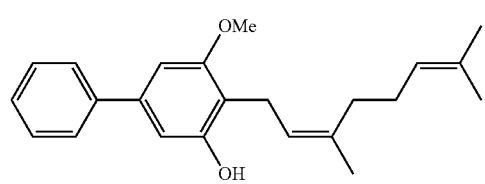
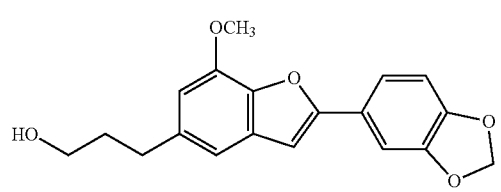
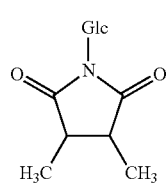
pharmaceutically acceptable salts, hydrates, and combinations thereof.
In other embodiments, the present invention provides methods of treatment or prophylaxis comprising administering a compound which is isolated or sourced from a plant extract selected from the group consisting of:
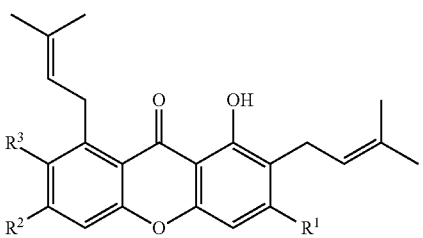
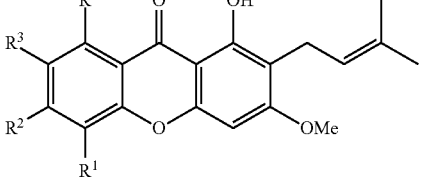
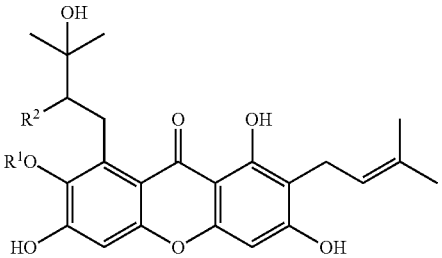
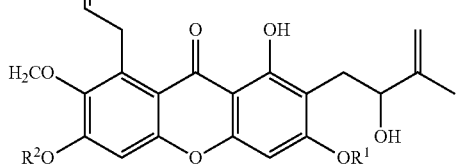
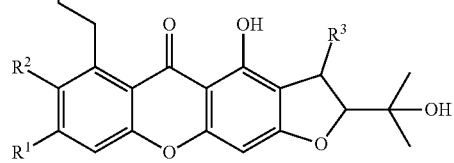
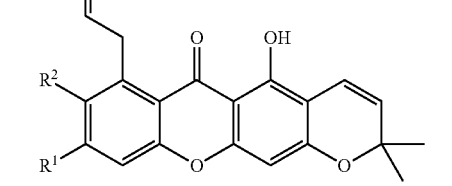
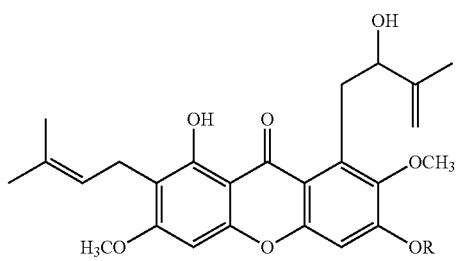

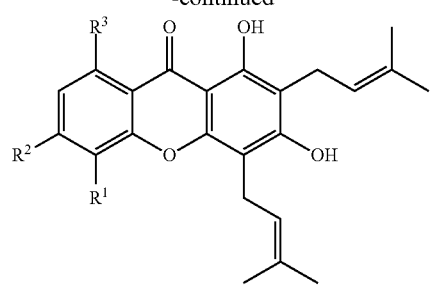
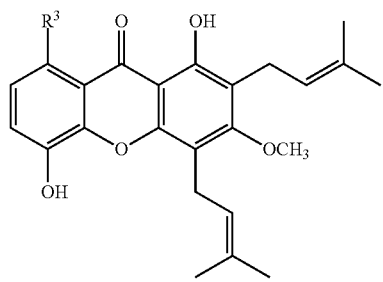
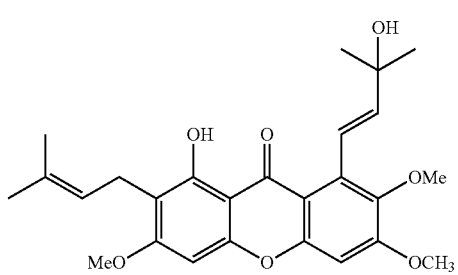
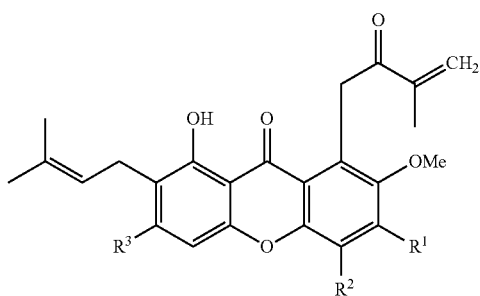
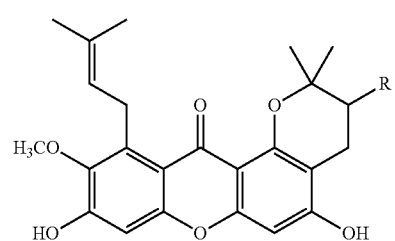
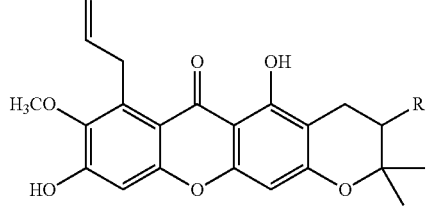
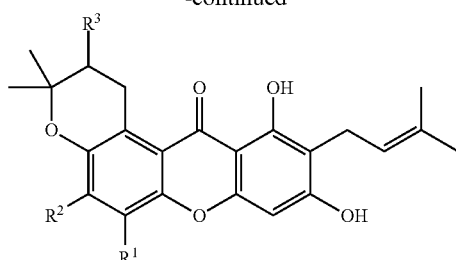
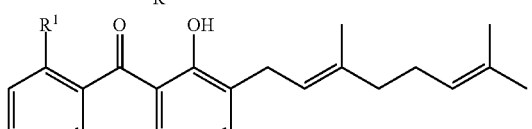
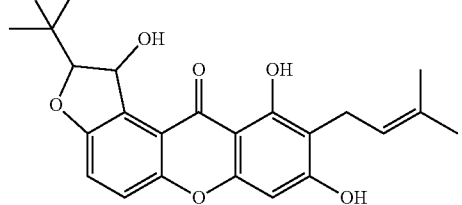
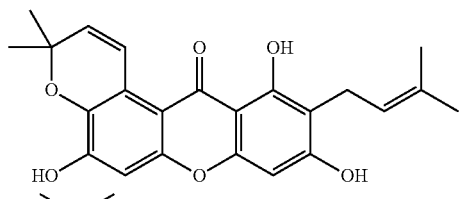
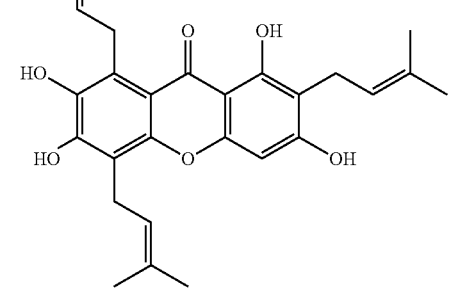
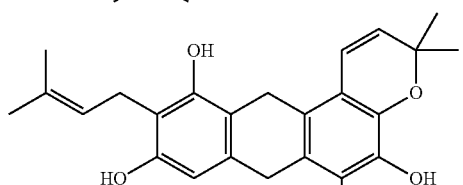
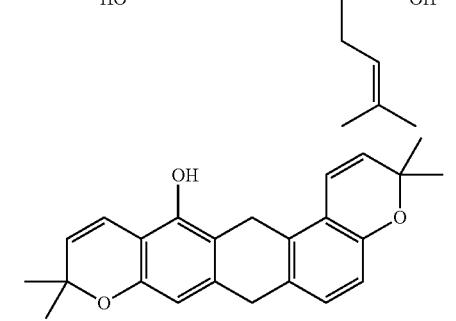

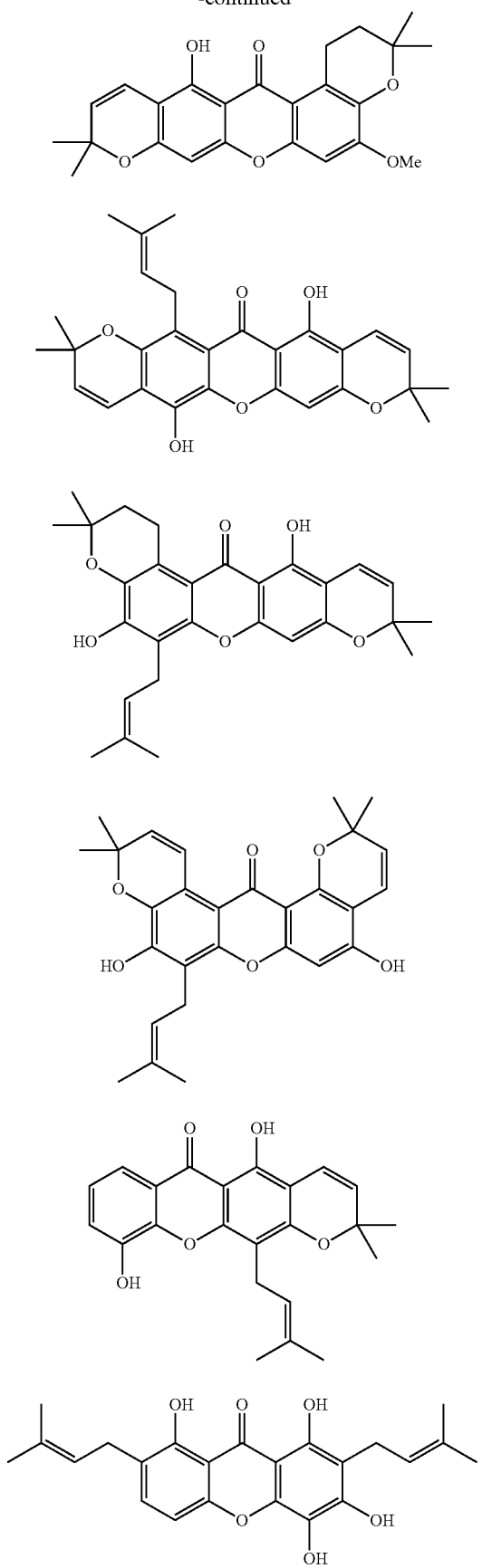
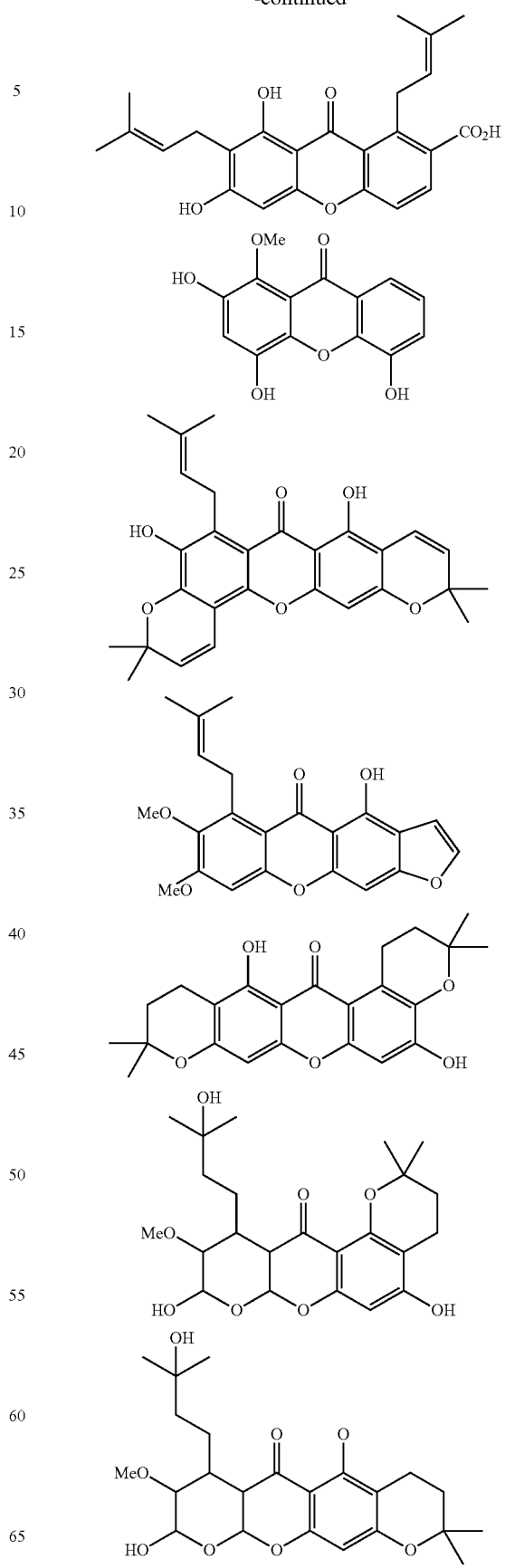

35
-continued
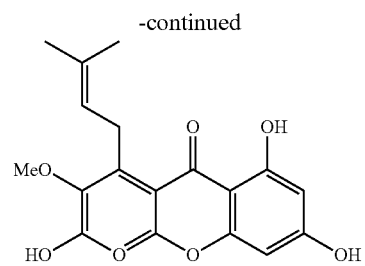
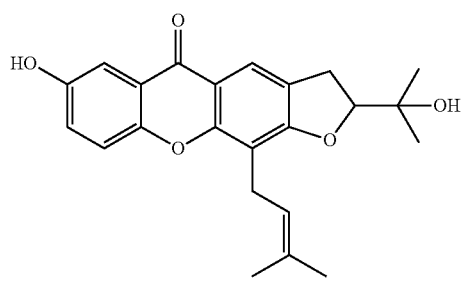
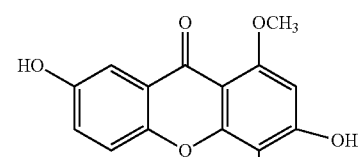
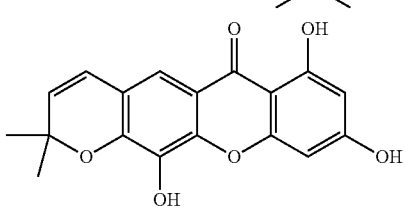
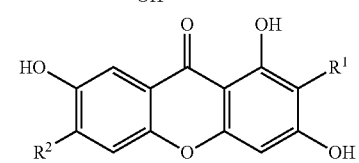
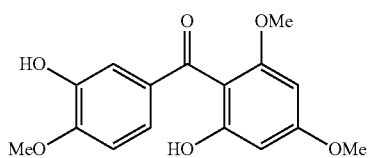
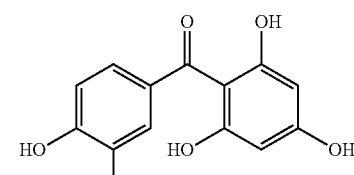
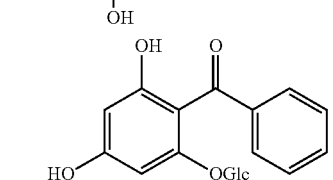
36
-continued
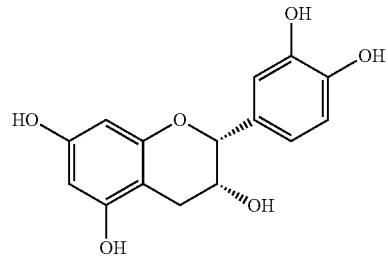
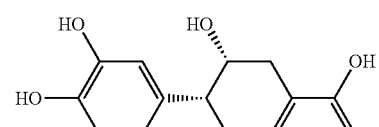
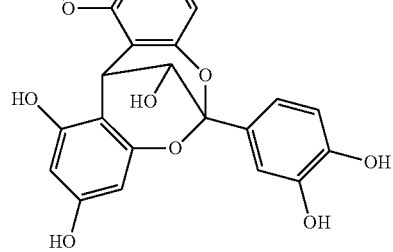
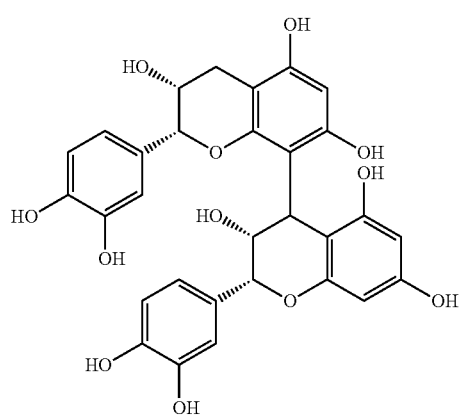
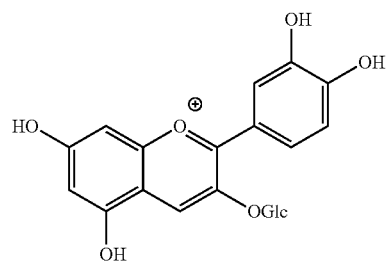
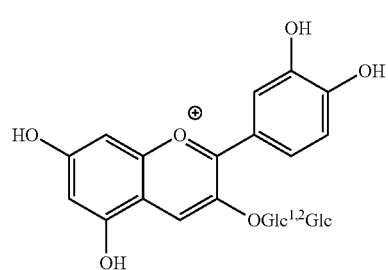

-continued
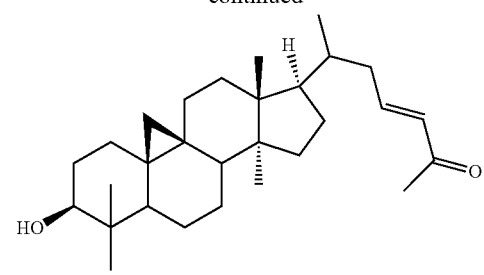
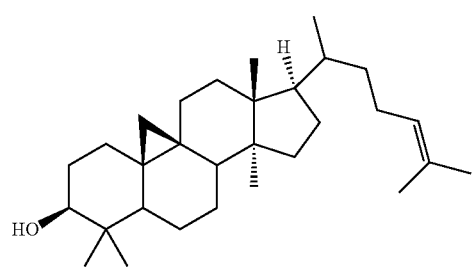
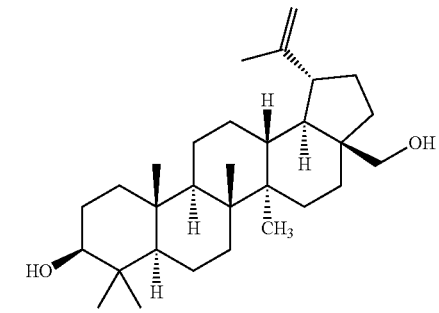
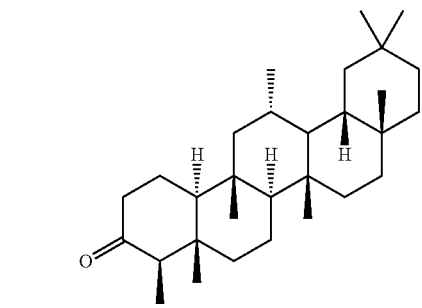
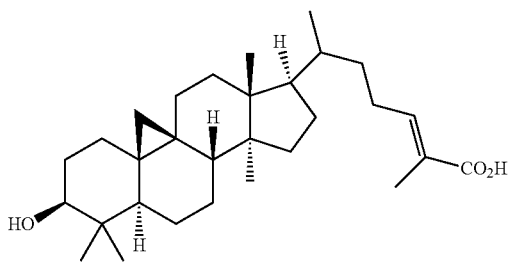
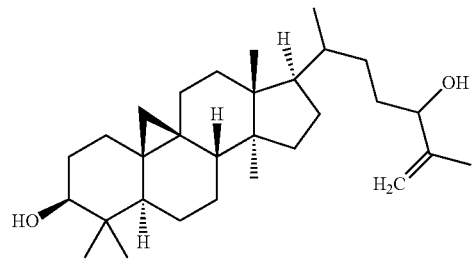
-continued
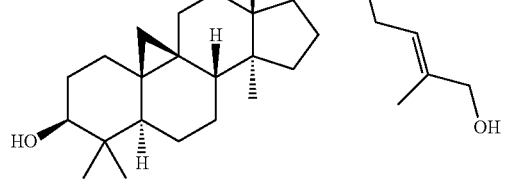
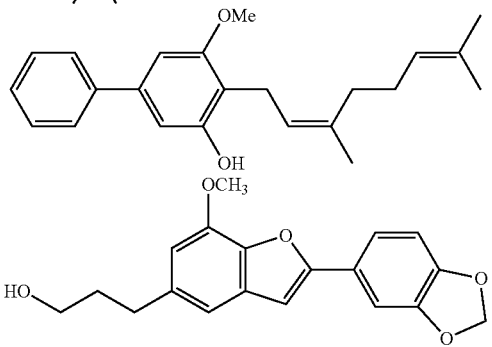
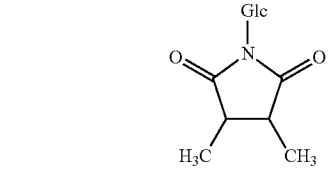
pharmaceutically acceptable salts, hydrates, and combinations thereof.
In other embodiments, the present invention provides methods of treatment or prophylaxis comprising administering a compound which is isolated or sourced from a plant extract, or a plant extract which includes a compound selected from the group consisting of:
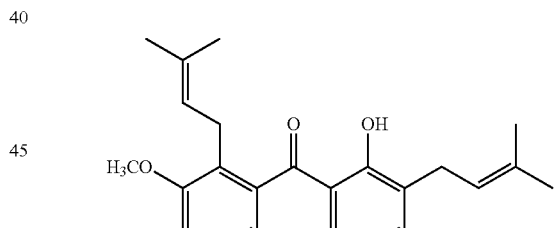
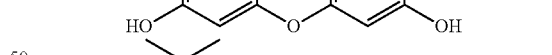
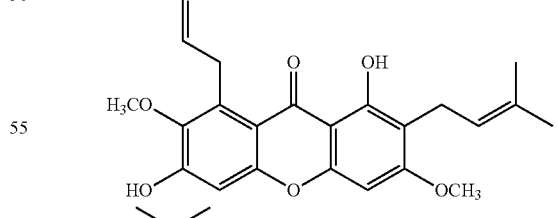
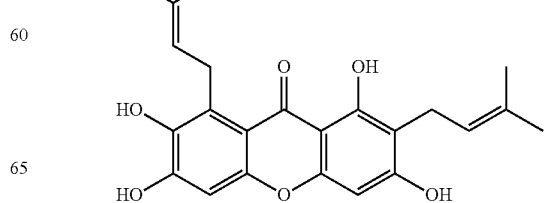

-continued

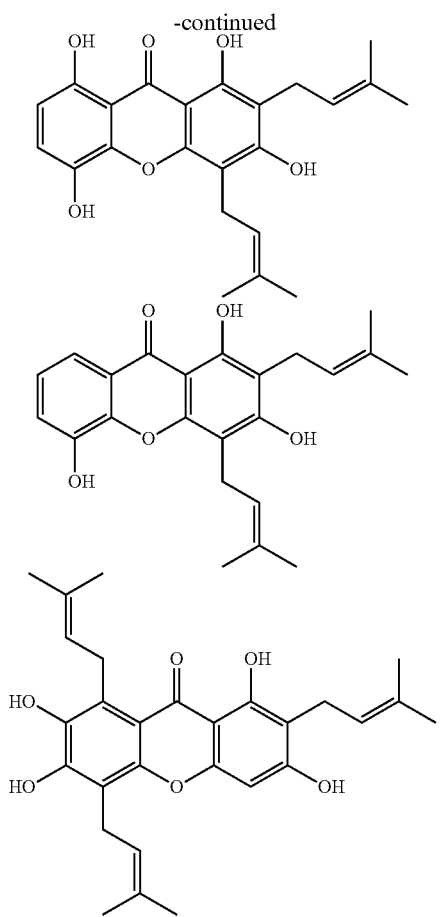

pharmaceutically acceptable salts, hydrates, and combinations thereof.

In other embodiments, the present invention provides methods of treatment or prophylaxis comprising administering α-mangostin or a plant extract comprising α-mangostin, of the following formula:

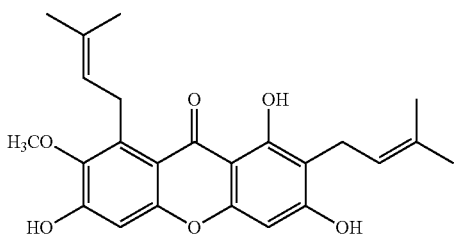 [SMILES: COc1c(O)cc2oc3cc(O)c(CC=C(C)C)c(O)c3c(=O)c2c1CC=C(C)C]

pharmaceutically acceptable salts and hydrates thereof.

Compounds suitable as therapeutic agents for administering in accordance with the methods of the present invention, can be prepared or isolated by procedures well known to those skilled in the art, for example, well known methods for preparing or isolating pluralities of compounds from plant extracts, including chemical or biological molecules such as simple or complex organic molecules, metal-containing compounds, carbohydrates, peptides, proteins, peptidomimetics, glycoproteins, lipoproteins, nucleic acids, antibodies, and the like, have been described the art.

For certain of the abovementioned conditions it is clear that the compounds may be used prophylactically as well as for the alleviation of acute symptoms. Accordingly, references herein to "treatment" or the like are to be understood to include such prophylactic treatment, as well as treatment of acute conditions.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Also provided herein are methods of treating or preventing central nervous system disorders, such as mood disorders (e.g., depression), anxiety disorders, or neurodegenerative diseases comprising the administration of an effective amount of a plant extract, especially an xanthone-rich plant extracts and their compounds isolated or sourced from a plant extract, or a pharmaceutically acceptable salt thereof, to a subject in need thereof.

As used herein mood disorders are broadly recognized and clearly defined by the relevant DSM-IV-TR (Diagnostic and Statistical Manual of Mental Disorders, $4^{th}$ Edition, Text Revision) criteria. Thus, there are depressive disorders, of which the best known and most researched is major depressive disorder (MDD) commonly called clinical depression or major depression, and bipolar disorder (BD), formerly known as manic depression and characterized by intermittent episodes of mania or hypomania, usually interlaced with depressive episodes. Other depressive disorders include: atypical depression, melancholic depression, psychotic major depression, catatonic depression, postpartum depression, seasonal affective disorder), dysthymia, depressive disorder not otherwise specified (DD-NOS) (e.g., recurrent brief depression, minor depressive disorder), substance induced mood disorders (e.g., alcohol induced mood disorders, benzodiazepine induced mood disorders, interferon-alpha induced mood disorders).

One of skill in the art will be familiar with the difficulties in administering traditional antipsychotic and antidepressant medications, including lag phases and heightened anxiety in the initial stages of treatment before the antidepressant effects are seen. Thus, in certain embodiments, it is envisaged that the plant extracts and compounds isolated or sourced from a plant extract described herein may be administered to a person in need thereof as a substitute or replacement for traditional antidepressant medication. In other embodiments, it is envisaged that the plant extracts and/or compounds isolated or sourced from a plant extract described herein may be administered to a subject in need thereof as a supplement or adjunct to traditional antidepressant medication. In still other embodiments, it is envisaged that the plant extracts and compounds isolated or sourced from a plant extract described herein, or a pharmaceutically acceptable salts thereof, may be administered to a person in need thereof in the absence of adjunct antidepressant therapy.

Replacing traditional medication with the plant extracts and/or compounds isolated or sourced from a plant extract as described herein may be advantageous, particularly where the traditional medication is associated with one or more adverse effects (e.g., anxiety, nausea, headaches, erectile dysfunction, early-onset suicidal tendencies, etc). Examples of traditional medication would be known to those skilled in the art and include, but are not limited to, antipsychotics, selective serotonin re-uptake inhibitors (SSRI), serotonin/noradrenalin re-uptake inhibitors, selective noradrenalin re-uptake inhibitors, monoamine oxidase inhibitors, tricyclic antidepressants, lithium and other mood stabilisers, atypical antidepressants, and hormones such as estrogen or progestogen.

In other embodiments, the present compounds are administered to a subject in need thereof, together with traditional medication for a discrete period of time, to address symptoms such as psychosis, depression or anxiety, with the option of discontinuing treatment with the present extracts and isolated compounds whilst continuing with the traditional therapy. In still other embodiments, the person in need thereof may be treated with both the plant extracts and/or compounds isolated or sourced from a plant extract described herein and one or more traditional medications (administered sequentially or in combination) for the duration of the treatment period. Such combination therapy may be particularly useful, for example, where an additive or synergistic therapeutic effect is desired.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of condition, or the amelioration of one or more symptoms (e.g., one or more discernable symptoms) of said condition (i.e., "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of a condition described herein. In other embodiments the terms "treat", "treatment" and "treating" refer to the inhibition of the progression of a condition described herein, either physically by, e.g., stabilization of a discernable symptom or physiologically by, e.g., stabilization of a physical parameter, or both.

The desired therapeutic activity, or effect, will typically depend on the condition being treated. For example, where the subject is being treated for schizophrenia, the therapeutic effect may be a reduction in at least one clinical symptom of schizophrenia, including, but not limited to, anxiety, suicidal thoughts, cognitive impairment, loss of appetite, mood, and/or inactivity.

The terms "preventing" and "prophylaxis" as used herein refer to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. As used in a standard text in the field, the Physician's Desk Reference, the terms "prevent", "preventing" and "prevention" with regard to a disorder or disease, refer to averting the cause, effects, symptoms or progression of a disease or disorder prior to the disease or disorder fully manifesting itself.

The plant extracts and/or compounds isolated or sourced from a plant extract of the present invention are administered to the person in need thereof in a treatment effective amount. In some embodiments, a treatment effective amount is a therapeutically effective amount or a prophylactically effective amount. The term "therapeutically effective amount" as used herein means that amount of an active compound, such as a plant extract or compound, or pharmaceutical agent that elicits the biological or medicinal response in a tissue, system, animal or human that is being sought by a researcher, veterinarian, medical doctor, or other clinician. The therapeutically effective amount of the compound to be administered will be governed by such considerations, and is the minimum amount necessary to ameliorate, cure, or treat the disease or disorder or one or more of its symptoms. The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease or symptom) and secondary prophylaxis (whereby the disease or symptom has already developed and the patient is protected against worsening of this process).

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 100 g per kg of body weight per dosage. The dosage may be in the range of 1 µg to 10 g per kg of body weight per dosage, such as is in the range of 1 mg to 1000 mg per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 200 mg per kg of body weight per dosage, such as up to 50 mg per body weight per dosage.

The terms "administer", "administering" or "administration" in reference to a compound, composition or formulation of the invention means introducing the extract or isolated compound into the system of the animal in need of treatment. When an extract or isolated compound of the invention is provided in combination with one or more other active agents, "administration" and its variants are each understood to include concurrent and/or sequential introduction of the compound and the other active agents.

In certain embodiments, an effective amount of a compound for administration one or more times a day to a 70 kg adult human may comprise about 0.0001 mg to about 4000 mg, about 0.0001 mg to about 3000 mg, about 0.0001 mg to about 200 mg, about 0.001 mg to about 1500 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an extract or compound per unit dosage form.

In certain embodiments, the extracts and/or compounds of the invention may be at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect.

Suitable dosage amounts and dosing regimens can be determined by the attending physician and may depend on the particular condition being treated, the severity of the condition as well as the general age, health and weight of the subject. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The plant extracts and/or compounds isolated or sourced from a plant extract of the present invention may be administered in a single dose or a series of doses. While it is possible for the extract and/or compound to be administered alone, in some embodiments it may be preferable to present it as a composition, preferably as a pharmaceutical composition. The formulation of such compositions is well known to those skilled in the art. Such a composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The plant extracts and/or compounds isolated or sourced from a plant extract and associated pharmaceutical compositions of the present invention may be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another anti-psychotic, anti-anxiety or anti-depressant medication, an "effective amount" of the second agent will depend on the type of drug used. Suitable dosages are known for approved agents and can be adjusted by a person skilled in the art according to the condition of the subject, the type of condition(s) being treated and the amount of a compound, extract or composition being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

The phrase "combination therapy" as used herein, is understood to refer to administration of an effective amount, using a first amount of a plant extract or a compound sourced from a plant extract or a pharmaceutically acceptable salt thereof as described herein, and a second amount of an additional suitable therapeutic agent.

In certain embodiments, the plant extracts and/or compounds isolated or sourced from a plant extract as described herein, or a pharmaceutically acceptable salt thereof, and the additional therapeutic agent, each administered in an effective amount (i.e., each in an amount which would be therapeutically effective if administered alone). In other embodiments, the plant extracts and/or compounds isolated or sourced from a plant extract as described herein, or a pharmaceutically acceptable salt thereof, and the additional therapeutic agent are each administered in an amount which alone does not provide a therapeutic effect (a sub-therapeutic dose). In yet other embodiments, the plant extracts and/or compounds isolated or sourced from a plant extract as described herein, or a pharmaceutically acceptable salt thereof can be administered in an effective amount, while the additional therapeutic agent is administered in a sub-therapeutic dose. In still other embodiments, the plant extracts and/or compounds isolated or sourced from a plant extract as described herein, or a pharmaceutically acceptable salt thereof, can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a person in need thereof.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of a plant extract and/or isolated component compound as described herein, or a pharmaceutically acceptable salt thereof, and a second amount of an additional therapeutic agent, they are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life, and kinetic profile. For example, a plant extract and/or isolated component compound as described herein, or a pharmaceutically acceptable salt thereof, and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Examples of second therapeutic agents that may be combined with a plant extract and/or isolated component compound of the present invention, either administered separately or in the same pharmaceutical composition, include, but are not limited to, muscle relaxants, antipsychotics, antidepressants, anticonvulsants, hypnotics, anaesthetics, analgesics, cholinergics, mood stabilisers, and anxiolytics, or combinations thereof.

In some embodiments, the second therapeutic agent may be is selected from the group consisting of Stelazine (Trifluoperazine), Flupenthixol (Fluanxol), Loxapine (Loxapac, Loxitane), Perphenazine (Etrafon, Trilafon), Chlorpromazine (Thorazine), Haldol (Haloperidol), Prolixin (Fluphenazine Decanoate, Modecate, Permitil), Aripiprazole (Abilify), Clozaril (clozapine), Geodon (ziprasidone), Risperdal (resperidone), Seroquel (Quetiapine), Zyprexa (olanzapine).

The plant extract and/or compound isolated from a plant extract provided herein may be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically, contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In particular embodiments, the plant extract and/or component compound of the present invention are administered orally.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

Where a carrier is used, the carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous, and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

In some embodiments, where the plant extract or component compound of the present invention is for oral administration, it may be prepared as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The plant extract or component compound may also be presented as a bolus, electuary or paste.

In some embodiments, where the plant extract or component compound of the present invention is formulated as a tablet, the tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., inert diluent, preservative disintegrant (e.g., sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

In some embodiments, the plant extract or component compound of the present invention may be in micro-encapsulated form with one or more excipients. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner Examples of embedding compositions which can be used include polymeric substances and waxes.

In some embodiments, where the plant extract or component compound of the present invention is to be administered as a liquid dosage forms for oral and parenteral administration, such a dosage form may include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

In some embodiments, where the plant extract or component compound of the present invention is to be administered topically in the mouth, suitable dosage forms may include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

In some embodiments, where the plant extract or component compound of the present invention is to be administered topically to the skin, suitable dosage forms may include the dissolving or suspending the extract or component compound in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol, and water. Transdermal patches may also be used to administer the extract or component compound of the invention.

In some embodiments, the plant extract or component compound of the present invention is for rectal administration, suitable dosage forms may include a suppository with a suitable base comprising, for example, cocoa butter, glycerin, gelatine or polyethylene glycol.

In some embodiments, where the plant extract or component compound of the present invention is for vaginal administration, suitable dosage forms may include pessaries, tampons, creams, gels, pastes, foams or spray formulations containing in addition to the active ingredient such carriers as are known in the art to be appropriate.

In some embodiments, where the plant extract or component compound of the present invention is for parenteral administration, suitable dosage forms may include aqueous and non-aqueous isotonic sterile injection solutions which may contain antioxidants, buffers, bactericides and solutes which render the composition isotonic with the blood of the intended recipient; and aqueous and non-aqueous sterile suspensions which may include suspending agents and thickening agents. The plant extract or component compound may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described. An injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In certain embodiments, unit dosage compositions are those containing a daily dose or unit, daily sub-dose, as herein above described, or an appropriate fraction thereof, of the active ingredient.

It should be understood that in addition to the active ingredients particularly mentioned above, the plant extracts or component compounds of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The phrase "pharmaceutically acceptable salt," as used herein, refers to pharmaceutically acceptable organic or inorganic salts of a provided compound. For use in medicine, the salts of the provided compounds will be pharmaceutically acceptable salts. Other salts may, however, be useful in the preparation of provided compounds or of their pharmaceutically acceptable salts. Pharmaceutically acceptable salts are well known in the art. For example, Berge et al., describe pharmaceutically acceptable salts in detail in *J. Pharm. Sci.* (1977) 66:1-19, incorporated herein by reference in its entirety. A pharmaceutically acceptable salt involves the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. When multiple charged atoms are present in the parent drug, its pharmaceutically acceptable salts will have multiple counter ions and these can be several instances of the same counter ion or different counter ions. Hence, a pharmaceutically acceptable salt can have one or more charged atoms in the parent compound and/or one or more counter ions.

Pharmaceutically acceptable salts of the component compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When a provided compound is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. Quaternary ammonium salts such as $N^+(C_{1-4}\text{ alkyl})_4$ are also included.

The preparation of the pharmaceutically acceptable salts described above and other typical pharmaceutically acceptable salts is more fully described by Berge et al., "Pharmaceutical Salts," *J. Pharm. Sci.,* 1977:66:1-19.

The formulations of the plant extract or component compound described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

It will be appreciated that any compound that is a prodrug of a component compound of the plant extracts of the present invention, is also within the scope and spirit of the invention. The term "pro-drug" is used in its broadest sense and encompasses those derivatives that are converted in vivo to the compounds of the invention. Such derivatives would readily occur to those skilled in the art.

The plant extracts or component compounds of the invention may be in crystalline form either as the free compounds or as solvates (e.g., hydrates) and it is intended that both forms are within the scope of the present invention. Methods of solvation are generally known within the art.

It will also be recognised that component compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, e.g., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

As used herein, the term "derived from" shall be taken to indicate that a particular integer or group of integers has originated from the species specified, but has not necessarily been obtained directly from the specified source. In respect of a compound(s) derived from plant extracts, it is understood that the particular compound(s) originated from a given plant or plant extract, but have not necessarily been obtained directly from the specified source.

Those skilled in the art will be aware that the invention described herein is subject to variations and modifications other than those specifically described. It is to be understood that the invention described herein includes all such variations and modifications. The invention also includes all such steps, features, methods, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Certain embodiments of the invention will now be described with reference to the following examples which are intended for the purpose of illustration only and are not intended to limit the scope of the generality hereinbefore described.

EXAMPLES

Example: Clinical Trial

Selection of Participants

Participants were recruited via advertisement, and referred to a treating physician for screening. Physicians screen persons for DSM-IV-TR criterion for i) schizophrenia; ii) current aggression risk; iii) ability to consent. Investigators conducted a preliminary interview with potential participants. Informed consent was obtained prior to inclusion in the trial. Participants were subsequently allocated a study number for trial identification purposes. A total of 80 persons meeting the DSM-IV-TR criteria for schizophrenia were recruited to take part in the trial. The clinical trial was registered under the Australian and New Zealand Clinical trial registry number; ACTRN12611000910909.

Intervention(s)/Treatment Group

Treatment group self-administered a *Garcinia mangostana* L. extract; that is, mangosteen dried fruit pericarp encapsulated in gelatine capsules as two 500 mg capsules, once a day (total 1000 mg/day) with food, for a period of 180 days. In certain Figures, the intervention/treatment group is referred to as Group 2.

Comparator/Control Group

Control group self-administered a placebo comprising rice flour weighted gelatine capsules as two 500 mg capsules, once a day (total 1000 mg/day) with food, for a period of 180 days. In certain Figures, the control group is referred to as Group 1.

Adherent/Non-Adherent Patient Groups

29% of the total patient cohort acknowledged that they were regularly taking standard prescribed medication (i.e. antipsychotic drugs) for the duration of the trial. The remaining 71% of patients acknowledged poor or non-adherence to their standard prescribed medication (i.e. antipsychotic drugs) for the duration of the trial. Rates of non-adherence were comparable between the placebo and mangosteen groups. The pattern of efficacy observed across entire patient cohort was also evident in those individuals who were non-adherent to their standard prescribed medication; that is, significant differences in treatment outcome were observed between the treatment group and control group in both the adherent and non-adherent patients. These results support both the primary efficacy and adjunctive efficacy of the claimed therapies.

Time Periods for Assessment

Assessment of certain criteria was conducted prior to commencement (0 months, baseline) and three time points thereafter; 3 months, 5 months, 6 months. Other criteria were assessed prior to commencement (0 months, baseline), and at conclusion (6 months).

Positive and Negative Symptom Scale (PANSS); Measured at Time Points Baseline (0 Months), 3 Months, 5 Months, 6 Months The Positive and Negative Syndrome Scale (PANSS) total figure was the primary outcome measure to assess efficacy, the effect size and statistical significance.

The PANSS total scores at 180 days were 25.85% lower in the treatment group, which is an overall 18.24% lower than the control group at 180 days.

The results with respect to the entire patient cohort are presented in FIGS. 1 to 4. The effect size between groups is indicated by a partial eta squared of 0.733 and statistical significance is established as $p<0.0005$.

The results for patients who acknowledged non-adherence to their standard prescribed medication are presented in FIGS. 5 to 8. Over time the placebo and treatment groups exhibited differing function and behaviour. The effect of treatment with mangosteen pericarp was statistically significant across all PANSS measures. A planned comparison demonstrated that the rate of change from baseline to 180 days was greater in the pericarp group across all measures. A post-hoc comparison indicated that the groups were different at 90, 150 and 150 days across all measures.

Figure 25:
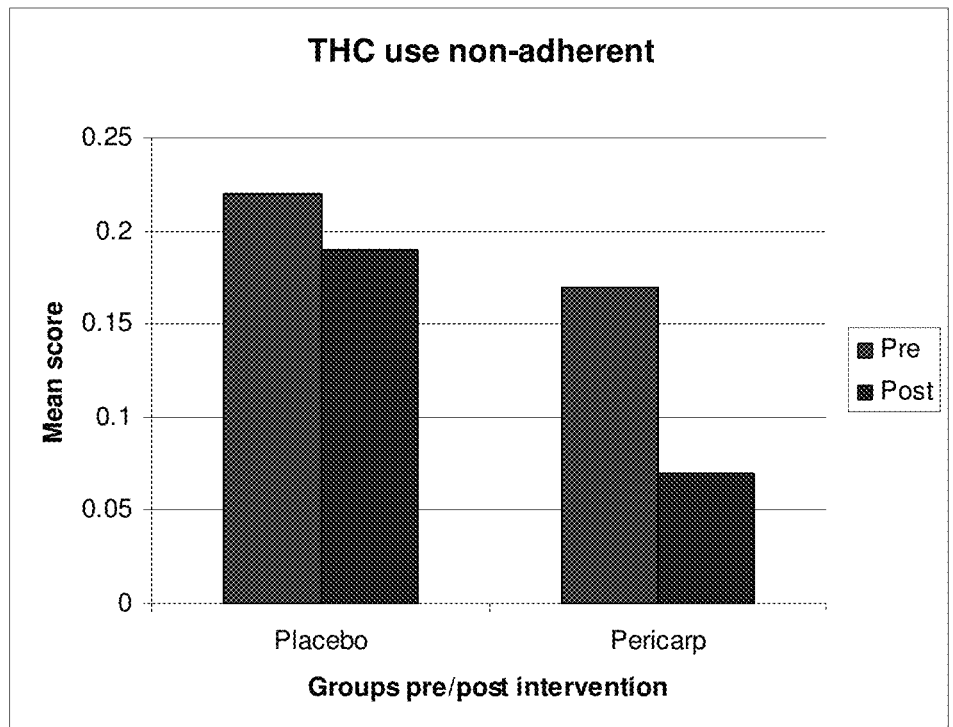
FIG. 25: No. of participants using *cannabis* in entire patient cohort; measured at two time points pre-intervention (0 months) and post-intervention (6 months).
Figure 26:
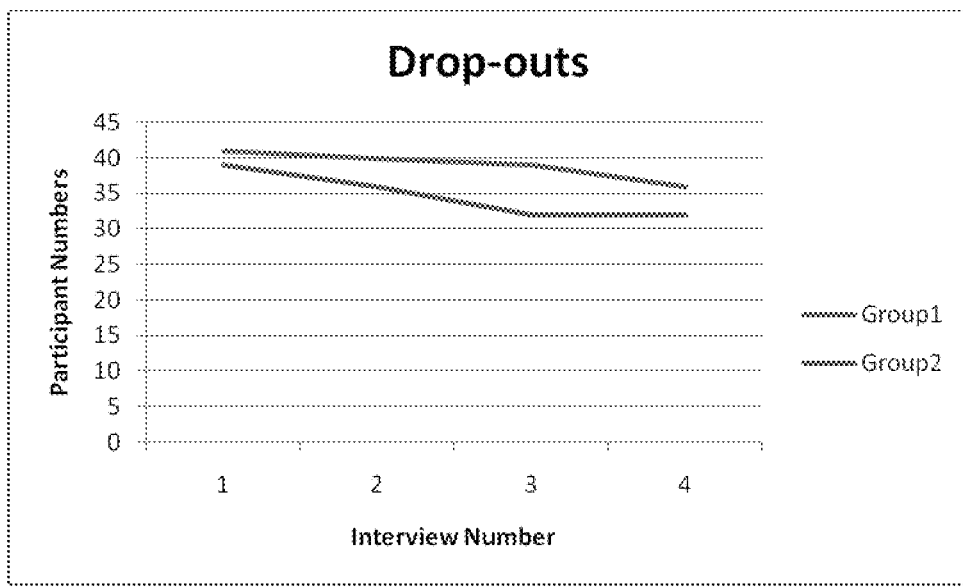
FIG. 26: Control reference No. of dropouts, measured by total no. interviews conducted at time points baseline (0 months), 3 months, 5 months, 6 months.

Despite non-adherence to their standard prescribed medications, the entire patient cohort demonstrated good compliance to either placebo or mangosteen pericarp intervention therapy. The placebo group took 98% of the prescribed intervention 95% of the time and the mangosteen pericarp group took 98% of the prescribed intervention 94% of the time (FIG. 25).

Montgomery and Asberg Depression Rating Scale (MADRS)

Figure 9:
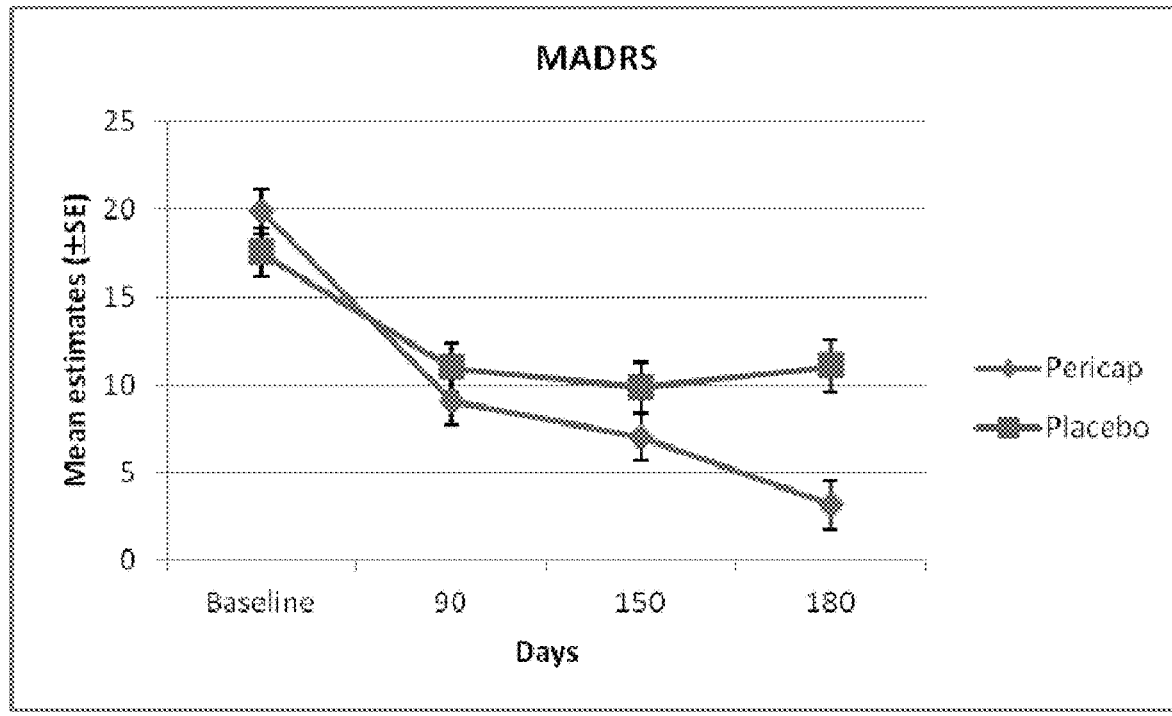
FIG. 9: Full patient cohort data for Montgomery and Asberg depression rating scale (MADRS); measured at time points baseline (0 months), 3 months, 5 months, 6 months. The Montgomery and Asberg Depression rating Scale (MADRS) for depression and suicidal ideations consist of 10 items on a scale 0 to 6. The lowest possible score was 0 and the highest is 60.
Figure 10:
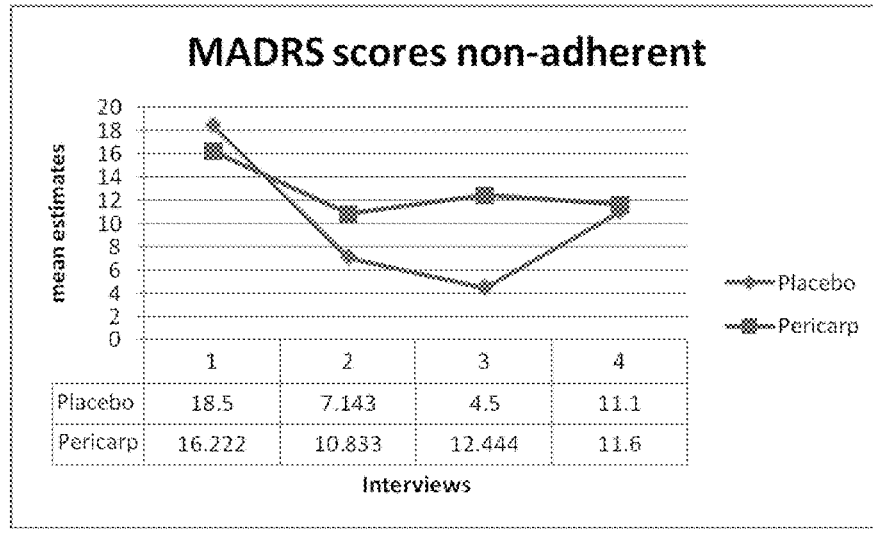
FIG. 10: Mean estimate scores of Montgomery and Asberg depression rating scale (MADRS) for patient cohort who acknowledged poor or non-adherence to standard prescribed medication, measured at time points baseline (0 months), 3 months, 5 months, 6 months. The Montgomery and Asberg Depression rating Scale (MADRS) for depression and suicidal ideations consist of 10 items on a scale 0 to 6. The lowest possible score was 0 and the highest is 60.

An assessment of the Montgomery and Asberg Depression rating Scale (MADRS) for depression and suicidal ideations was also conducted across the entire cohort of patients (FIG. 8) and non-adherent patients (FIG. 9). Overtime, for the non-adherent patient cohort the placebo and treatment groups were considered to function and/or behave similarly. according to this measure. A planned comparison demonstrated that the rate of change from baseline to 180 days was similar in both groups. A post-hoc comparison indicated that the groups were different at 90 and 150 days.

Liverpool University Neuroleptic Side Effect Rating Scale (LUNSERS)

Figure 11:
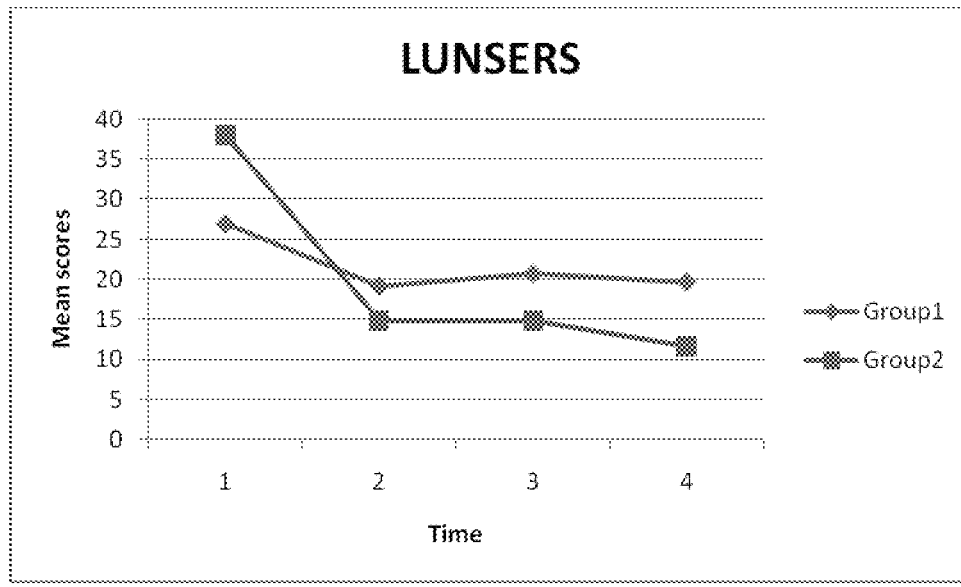
FIG. 11: Liverpool University neuroleptic side effect rating scale (LUNSERS) for full patient cohort; measured at time points baseline (0 months), 3 months, 5 months, 6 months.

Tolerance was set at 5% to enable assessment of common side effects gauged by Liverpool University neuroleptic Side Effect Rating Scale (LUNSERS) interview scores. The analysis involved testing two sub-groups of LUNSERS; i) antipsychotic side effects and ii) extrapyramidal side effects. The results with respect to the entire patient cohort are presented in FIG. 11. Data indicated that the treatment group had a 22.87% reduction in antipsychotic side effects compared to the control group at 180 days (p<0.02). Data further indicates, that the treatment had a 15.54% reduction in extrapyramidal side effects comparative to the control group at 180 days (p<0.028).

Figure 12:
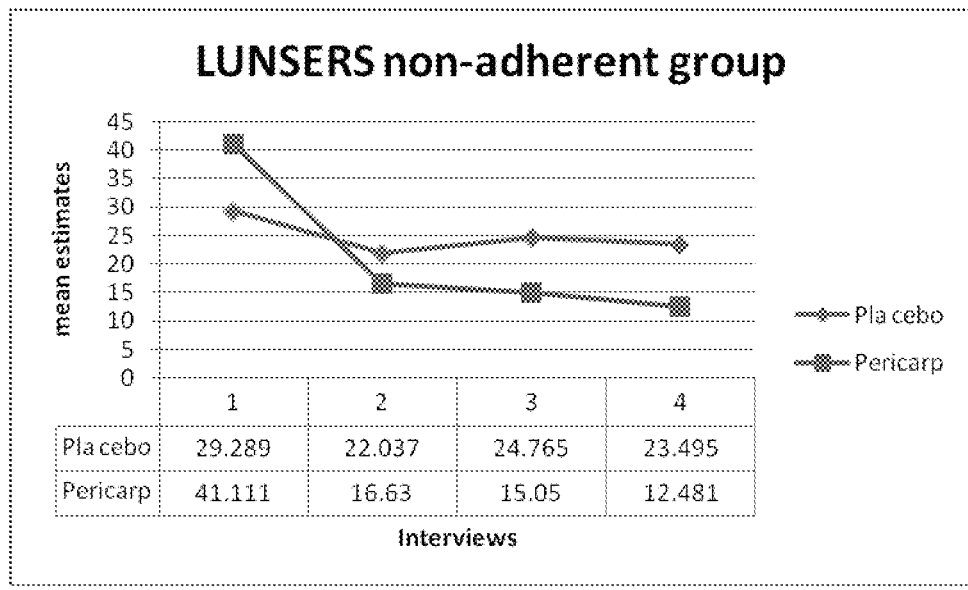
FIG. 12: Liverpool University neuroleptic side effect rating scale (LUNSERS) for patient cohort who acknowledged poor or non-adherence to standard prescribed medication; measured at time points baseline (0 months), 3 months, 5 months, 6 months.

The results for the sub-set of patients who acknowledged non-adherence to their standard prescribed medication are presented in FIG. 12. The LUNSERS scores for the non-adherent group using MMRM with post-hoc analysis were significantly different between groups at 180 days (p<0.01).

Global Assessment of Functioning (GAF)

Global assessment of functioning (GAF) was a measure of function., for example, an upward trending graph demonstrates improvements to functioning over time. The GAF scores are divided into increments of tens and range from 1-100. For the purpose of data entry the first number in the range was entered so that 10-1 became 10 for instance. The lowest possible score is therefore 10 and the highest possible score is 100.

Figure 13:
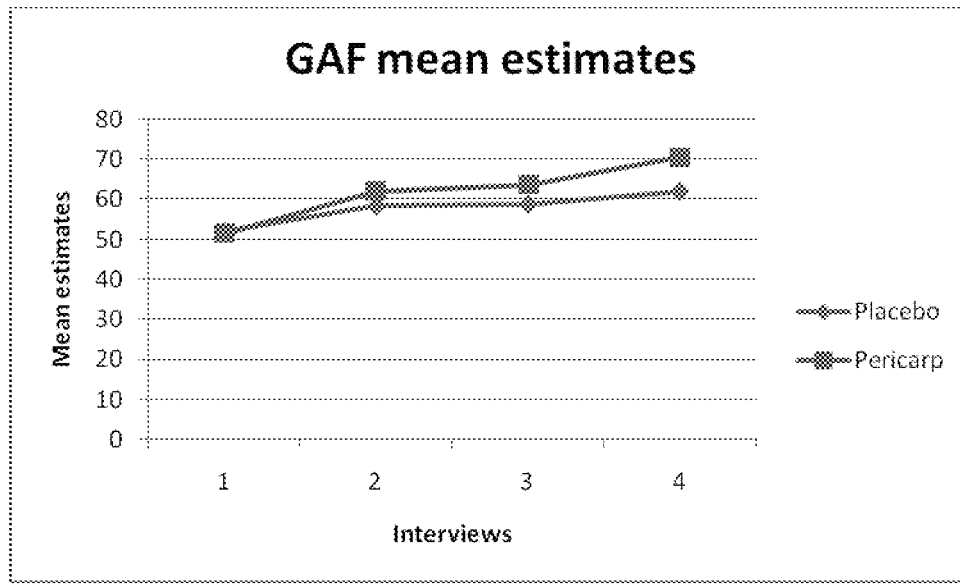
FIG. 13: Clinical global impression scale (GAF) for full patient cohort, measured at time points baseline (0 months), 3 months, 5 months, 6 months. GAF scores are divided into increments of tens and range from 10-100. The lowest possible score is 10 and the highest possible score is 100.
Figure 14:
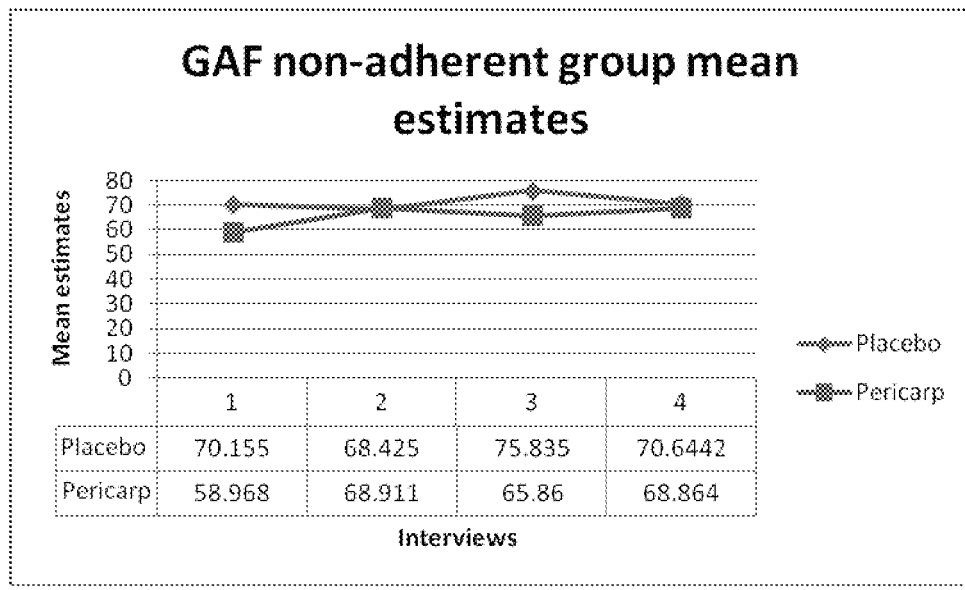
FIG. 14: Clinical global impression scale (GAF) for patient cohort who acknowledged poor or non-adherence to standard prescribed medication, measured at time points baseline (0 months), 3 months, 5 months, 6 months. GAF scores are divided into increments of tens and range from 10-100. The lowest possible score is 10 and the highest possible score is 100.

The results with respect to the entire patient cohort are presented in FIG. 13. The results for the sub-set of patients who acknowledged non-adherence to their standard prescribed medication are presented in FIG. 14.

The Self-Rated Life Satisfaction (SRLS)

The Self-Rated Life Satisfaction (SRLS) score was used to measure of quality of life. Scores range from 1 to 5 across four questions. The lowest possible score is 4 and the highest possible is 20. Scores above 12 are concurrently associated with depressive symptoms.

Figure 15:
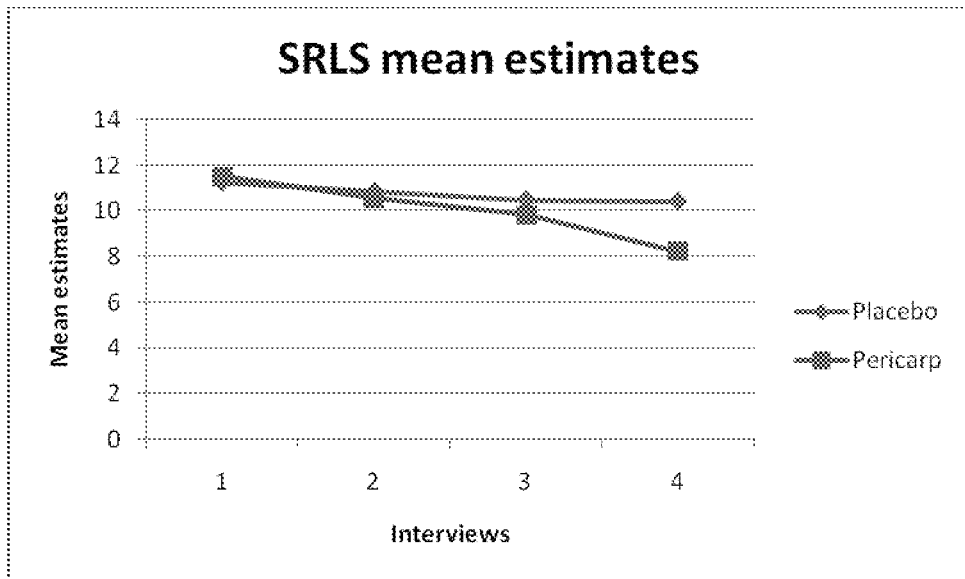
FIG. 15: Self-rated life satisfaction scale (SRLS) for full patient cohort, measured at time points baseline (0 months), 3 months, 5 months, 6 months. Scores range from 1-5 across four questions. The lowest possible score is 4 and the highest possible is 20. Scores above 12 are concurrently associated with depressive symptoms.
Figure 16:
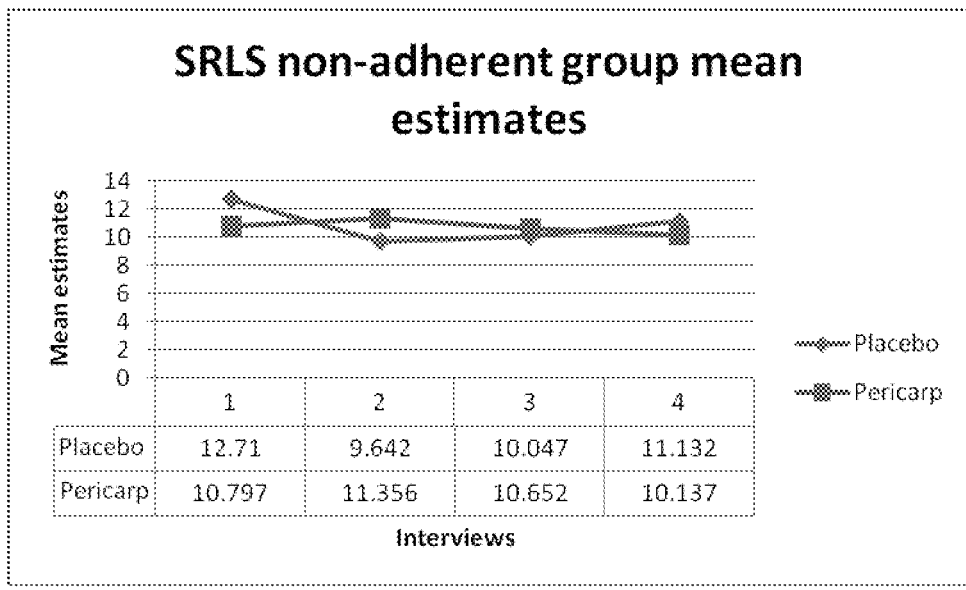
FIG. 16: Self-rated life satisfaction scale (SRLS) for patient cohort who acknowledged poor or non-adherence to standard prescribed medication, measured at time points baseline (0 months), 3 months, 5 months, 6 months. Scores range from 1-5 across four questions. The lowest possible score is 4 and the highest possible is 20. Scores above 12 are concurrently associated with depressive symptoms.

The results with respect to the entire patient cohort are presented in FIG. 15. The results for the sub-set of patients who acknowledged non-adherence to their standard prescribed medication are presented in FIG. 16.

Suicidal Ideation

Suicidal ideation is a sub-scale of Montgomery and Asberg Depression rating Scale (MADRS), assessing suicidal ideations only. The scale consists of items 0 to 6. The lowest score possible is 0 and the highest is 6.

Figure 17:
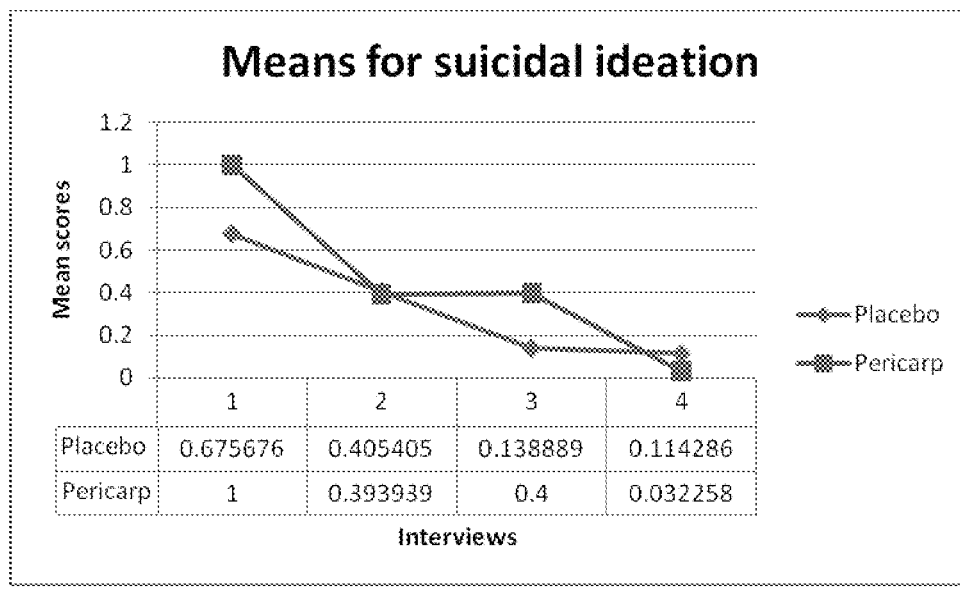
FIG. 17: Suicidal ideation for full patient cohort, measured at time points baseline (0 months), 3 months, 5 months, 6 months. The scale consists of items 0 to 6. The lowest score possible is 0 and the highest is 6.
Figure 18:
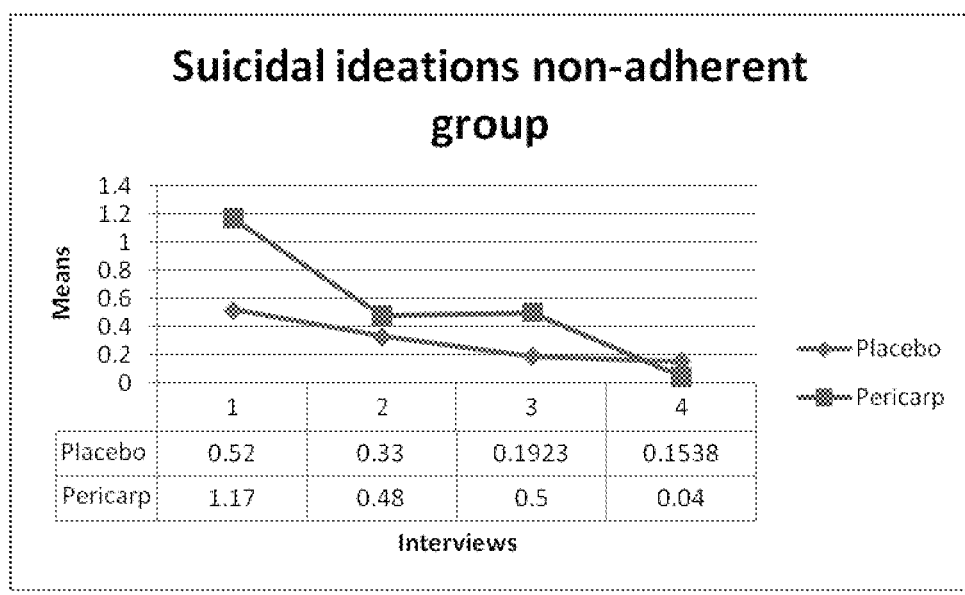
FIG. 18: Suicidal ideation for patient cohort who acknowledged poor or non-adherence to standard prescribed medication, measured at time points baseline (0 months), 3 months, 5 months, 6 months. The scale consists of items 0 to 6. The lowest score possible is 0 and the highest is 6.

The results with respect to the entire patient cohort are presented in FIG. 17. The results for the sub-set of patients who acknowledged non-adherence to their standard prescribed medication are presented in FIG. 18.

The Clinical Global Impression

Figure 19:
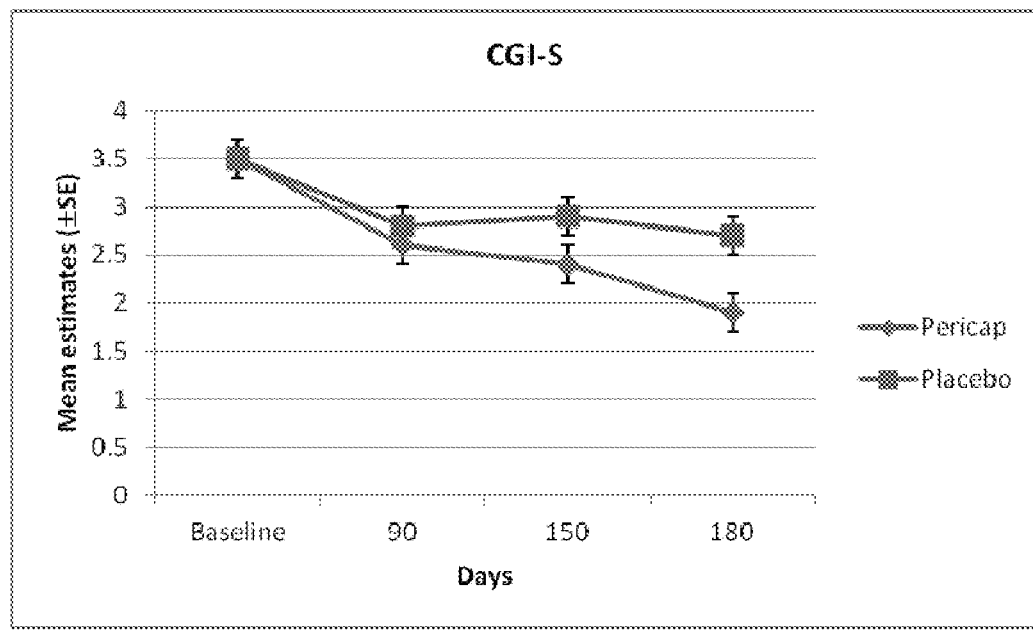
FIG. 19: The Clinical Global Impression-Severity scale (CGI-S) for full patient cohort, measured at time points baseline (0 months), 3 months, 5 months, 6 months. The scale consists of items 1 to 7, with the lowest score of 1 indicating a normal mental health states and the highest score of 7 indicating the patient is extremely ill.

The Clinical Global Impression Severity scale (CGI-S) is commonly used as a measure of symptom severity, treatment response and the efficacy of treatments in treatment studies of patients with mental disorders. Specifically, the severity of a patient's illness at the time of assessment is rated, relative to the assessing clinician's past experience with patients who have the same diagnosis. The scale consists of items 1 to 7, with the lowest score of 1 indicating a normal mental health states and the highest score of 7 indicating the patient is extremely ill. The results with respect to the entire patient cohort are presented in FIG. 19.

Tobacco, Alcohol and *cannabis* (THC) Consumption

Figure 20:
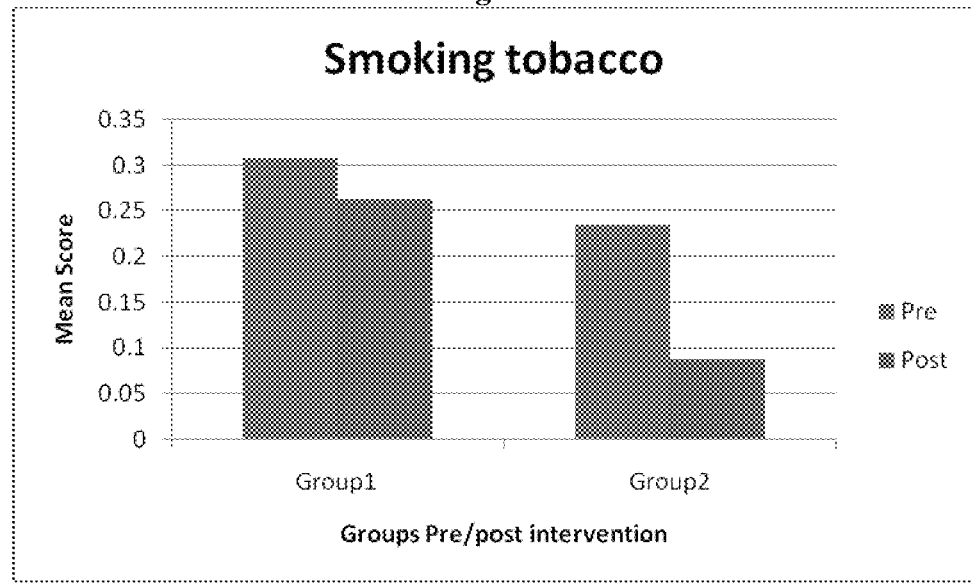
FIG. 20: No. of participants smoking tobacco in entire patient cohort; measured at two time points pre-intervention (0 months) and post-intervention (6 months).
Figure 21:
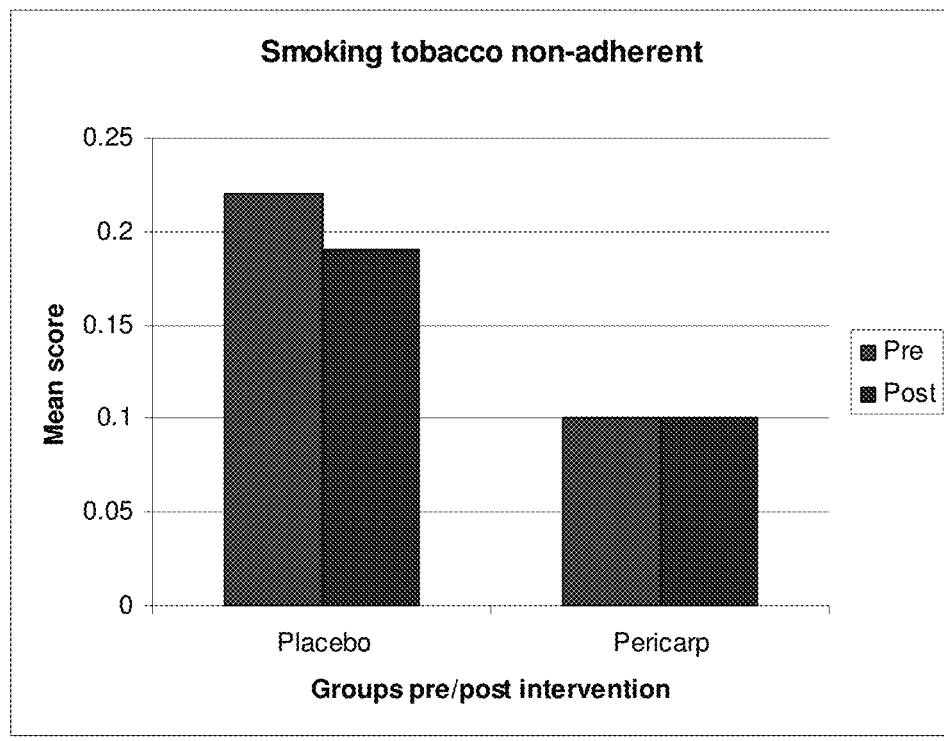
FIG. 21: No. of participants smoking tobacco in patient cohort who acknowledged poor or non-adherence to standard prescribed medication, measured at two time points pre-intervention (0 months) and post-intervention (6 months).
Figure 22:
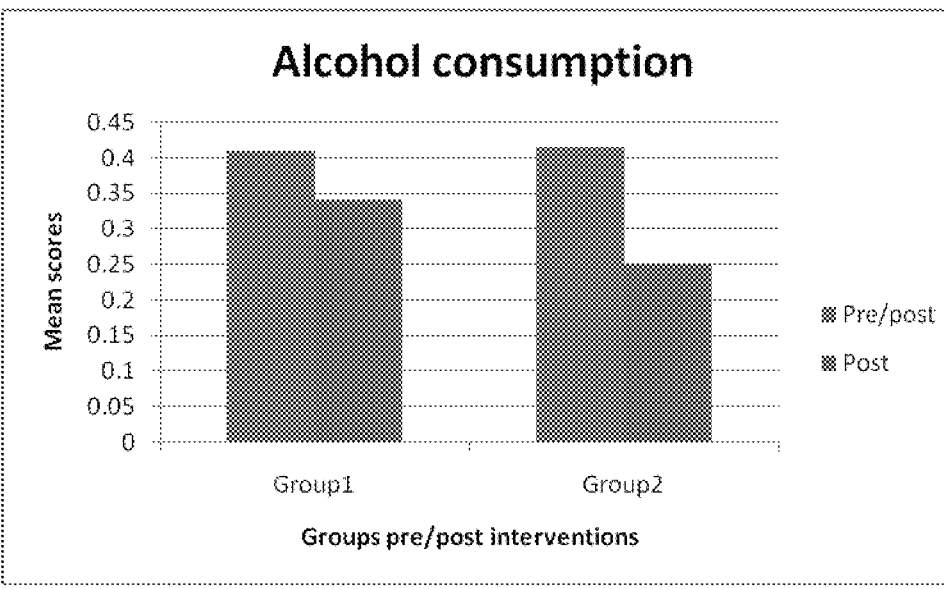
FIG. 22: No. of participants consuming alcohol in entire patient cohort; measured at two time points pre-intervention (0 months) and post-intervention (6 months).
Figure 23:
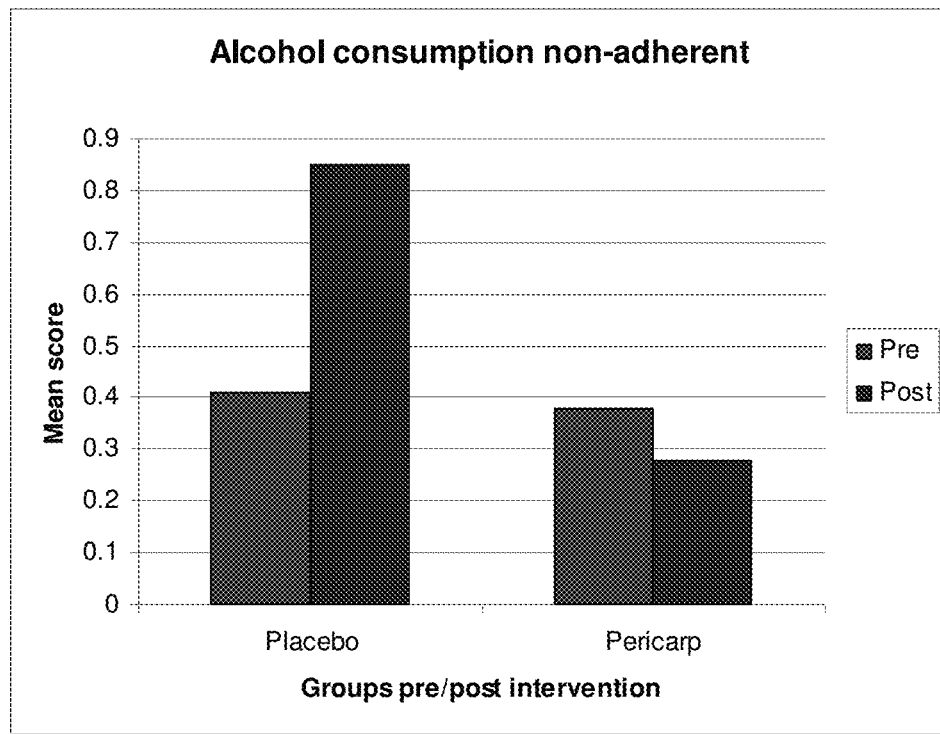
FIG. 23: No. of participants consuming alcohol in patient cohort who acknowledged poor or non-adherence to standard prescribed medication; measured at two time points pre-intervention (0 months) and post-intervention (6 months).
Figure 24:
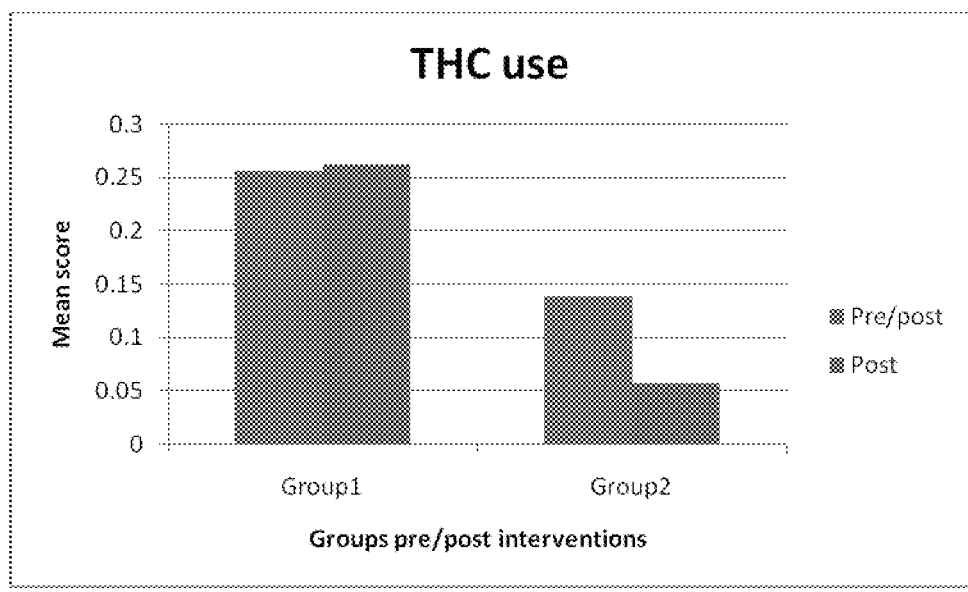
FIG. 24: No. of participants using *cannabis* in patient cohort who acknowledged poor or non-adherence to standard prescribed medication; measured at two time points pre-intervention (0 months) and post-intervention (6 months).

Patients were assessed with respect to their tobacco, alcohol and *cannabis* consumption. The results with respect to the entire patient cohort are presented in FIGS. 20, 22 and 24, respectively. The corresponding results for the sub-set of patients who acknowledged non-adherence to their standard prescribed medication are presented in FIGS. 21, 23 and 25.

REFERENCES

1) Do K Q, Trabesinger A H, Kirsten-Kruger M, Lauer C J, Dydak U, Hell D, Holsboer F, Boesiger P and Cuenod M., (2000), *Euro J Neurosci*, 12:3721-8;
2) Do K Q, Lauer C J, Schreiber W, Zollinger M, Gutteck-Amsler U, Cuenod M and Holsboer F., (1995), *J Neurochem*, 65:2652-62;
3) Abdalla D S, Monteiro H P, Oliveira J A and Bechara E J., (1986), *Clin Chem*, 32:805-7;
4) Buckman T D, Kling A S, Eiduson S, Sutphin M S and Steinberg A., (1987), *Biol Psychiatry*, 22:1349-56
5) Yao J K, Reddy R D and van Kammen D P., (1999), *Biol Psychiatry*, 45:1512-5;
6) Duffield A J, Thomson C D, Hill K E and Williams S., (1999), *Am J Clin Nutr*, 70:896-903;
7) Gurney M E, Cutting F B, Zhai P, Doble A, Taylor C P, Andrus P K and Hall E D., (1996), *Ann Neurol*, 39:147-57;
8) Huse, U.S. Pat. No. 5,264,563;
9) Francis et al., *Curr. Opin. Chem. Biol.*, 2:422-428 (1998);
10) Tietze et al., *Curr. Biol.*, 2:363-381 (1998);
11) Sofia, *Molecule. Divers.*, 3:75-94 (1998);
12) Eichler et al., *Med. Res. Rev.* 15:481-496 (1995)
13) Gordon et al., *J. Med. Chem.* 37:1233-1251 (1994);
14) Gordon et al., *J. Med. Chem.* 37:1385-1401 (1994);
15) Gordon et al., *Acc. Chem. Res.* 29:144-154 (1996);
16) Wilson and Czarnik, eds., *Combinatorial Chemistry: Synthesis and Application*, John Wiley & Sons, New York (1997);
17) Diagnostic and Statistical Manual of Mental Disorders, $4^{th}$ Edition, Text Revision
18) *Remington's Pharmaceutical Sciences*, Sixteenth Edition, E. W. Martin (Mack Publishing Co., Easton, Pa., 1980;
19) *Remington: The Science and Practice of Pharmacy*, 21st Edition (Lippincott Williams & Wilkins, 2005;
20) Berge et al., "Pharmaceutical Salts," *J. Pharm. Sci.*, 1977:66:1-19.

The invention claimed is:

1. A method for the treatment of schizophrenia, bipolar disorder, depression or anxiety comprising administering to a mammal in need thereof an effective amount of a xanthone-rich plant extract, wherein the plant extract is an extract from the pericarp of the fruit of Clusiaceae *Garcinia mangostana* (mangosteen), and wherein the plant extract comprises α-mangostin

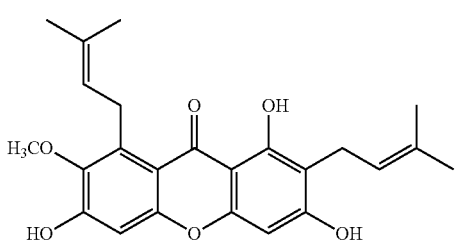 [SMILES: COc1c(O)cc2oc3cc(O)c(CC=C(C)C)c(O)c3c(=O)c2c1CC=C(C)C]

or a pharmaceutically acceptable salt, hydrate or combination thereof.

2. A method according to claim 1, wherein the disease or disorder is bipolar disorder.

3. A method according to claim 1, wherein the disease or disorder is schizophrenia.

4. A method according to claim 1, wherein the plant extract comprises one or more further compounds selected from the group consisting of xanthones, xanthenes, polyphenols, tannins, flavonoids, triterpenoids, benzophenones, biphenyl compounds, pyrroles, benzofurans, anthocyanins, procyannins, prodelphinidins, epicatechins, and combinations thereof.

5. A method according to claim 1, wherein the plant extract comprises one or more further compounds selected from the group consisting of:

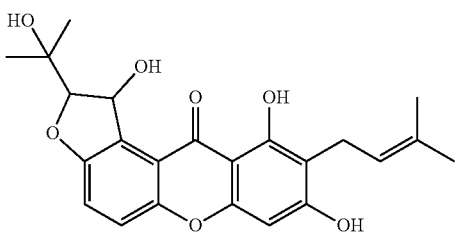

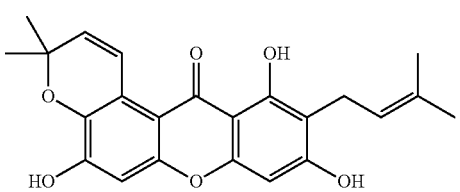

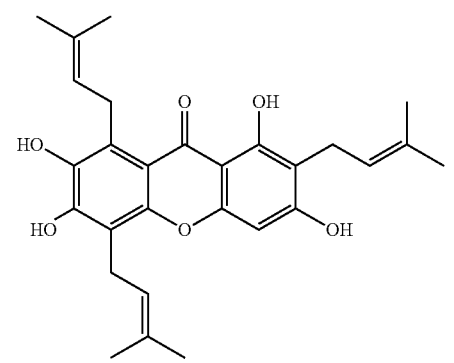

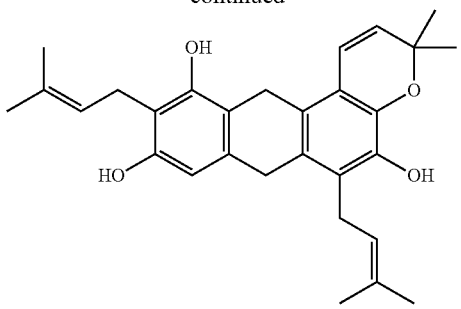

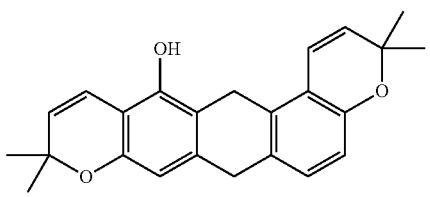

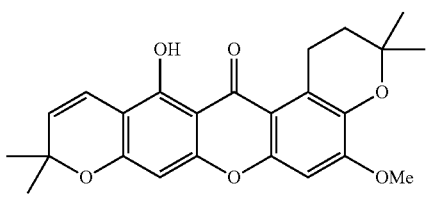

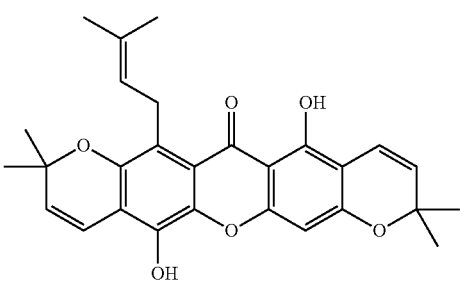

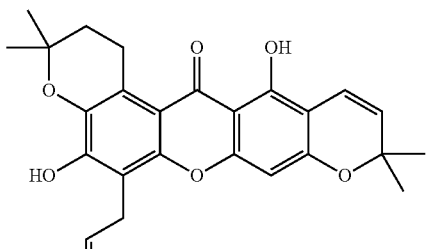

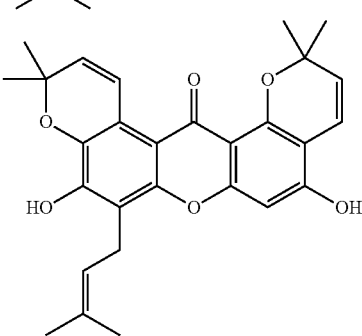

-continued
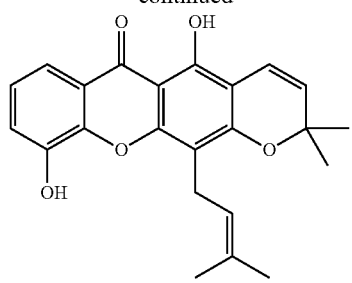
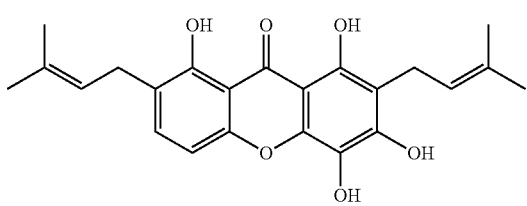
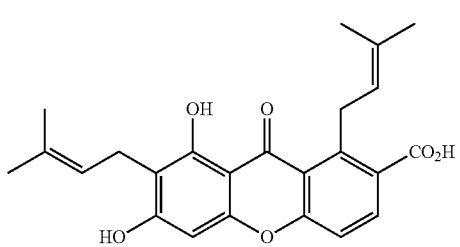
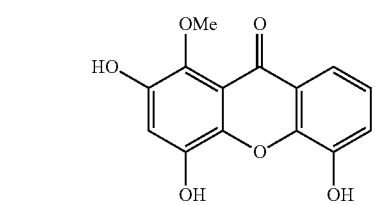
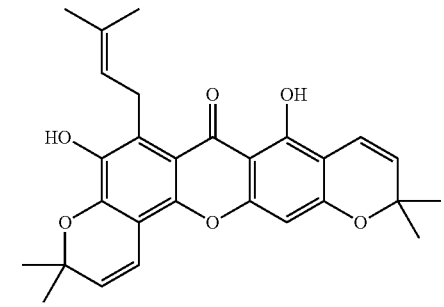
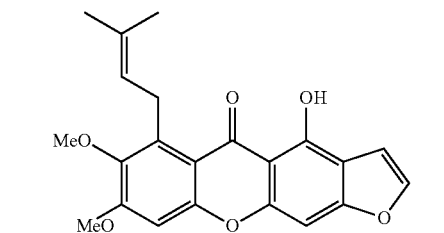
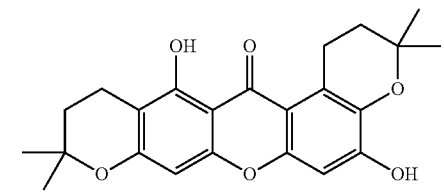
-continued
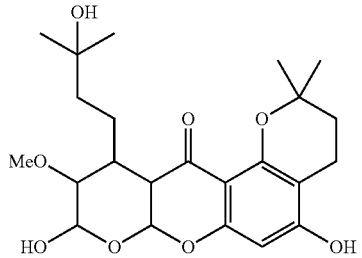
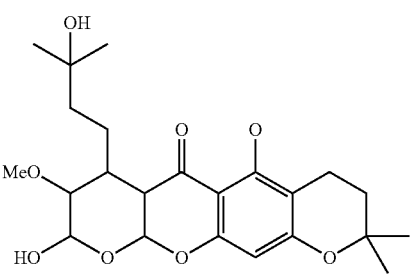
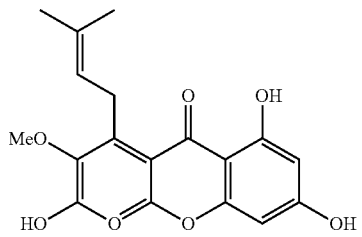
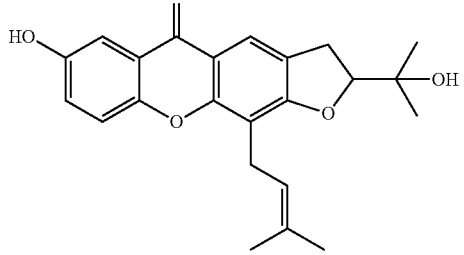
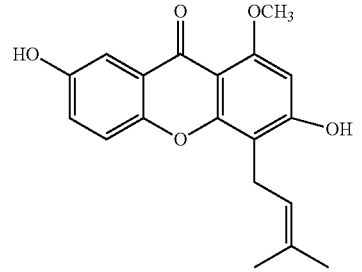
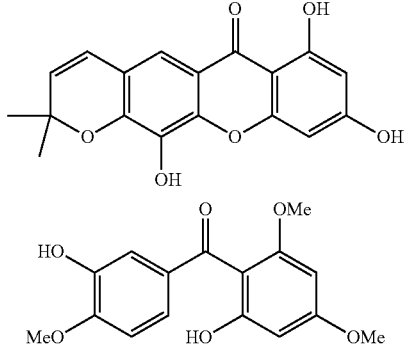

59
-continued
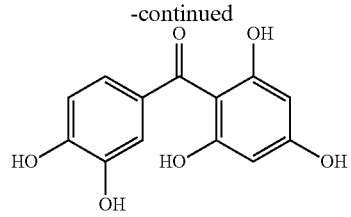
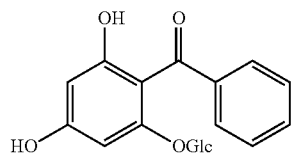
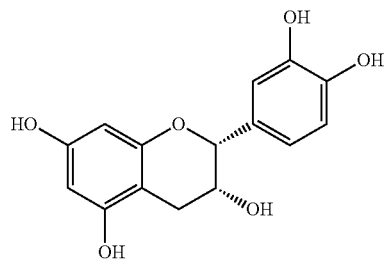
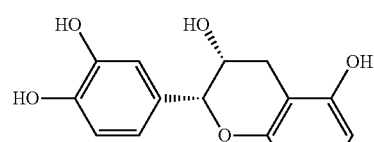
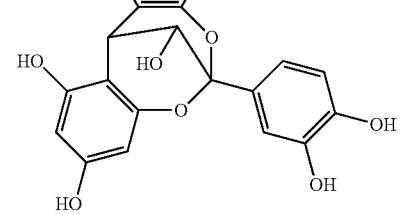
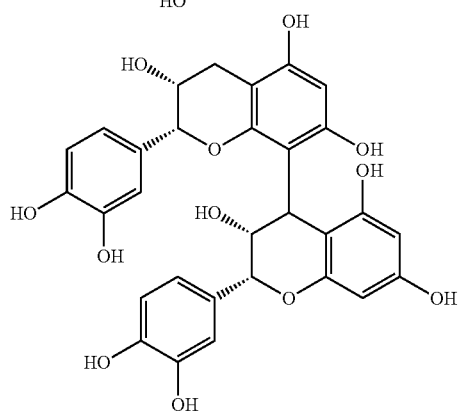
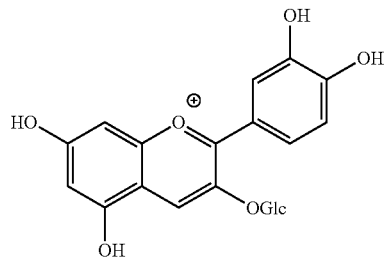
60
-continued
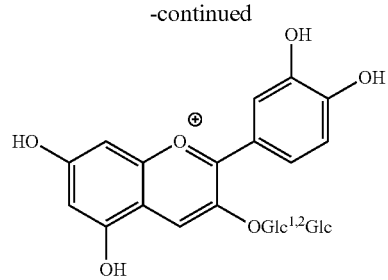
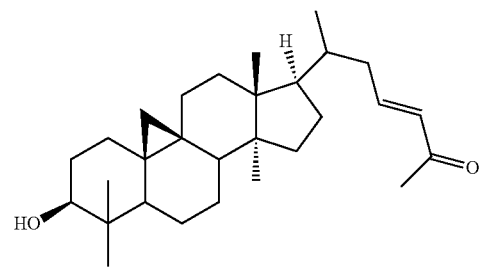
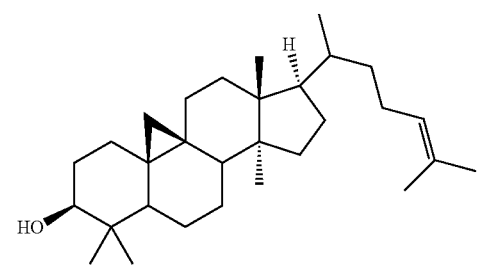
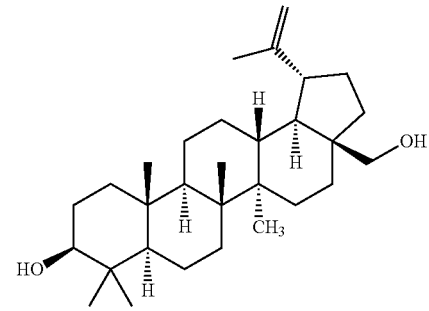
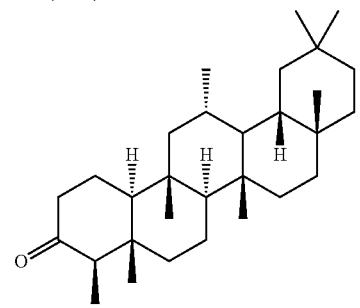
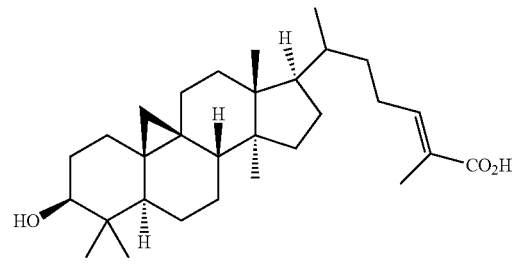

-continued

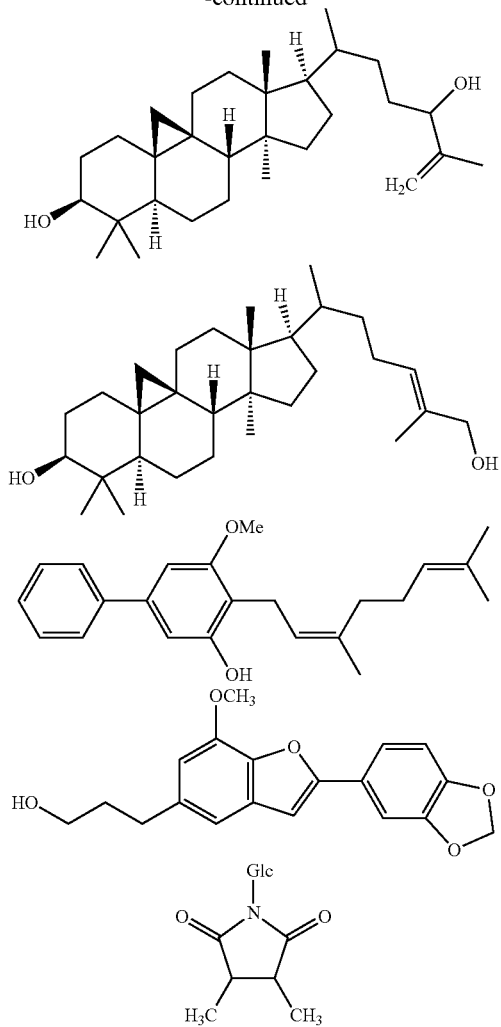

and pharmaceutically acceptable salts, hydrates, and combinations thereof.

6. A method according to claim 1, wherein the plant extract further comprises one or more compounds selected from the group consisting of:

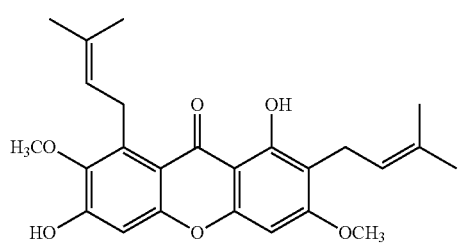

-continued

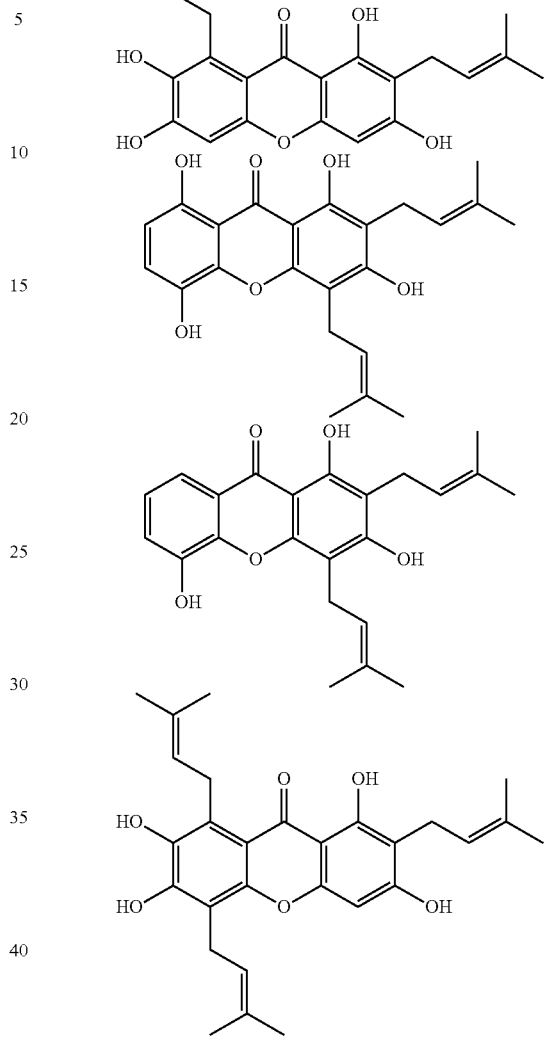

and pharmaceutically acceptable salts, hydrates, and combinations thereof.

7. A method according to claim 1, wherein the plant extract is administered in a dosage in the range of 0.01 to 6000 mg/day, 0.1 to 5000 mg/day, 1 to 4000 mg/day, 10 to 3000 mg/day, 100 to 2000 mg/day, or 500 to 1500 mg/day.

8. A method according to claim 1, wherein the plant extract is administered in a dosage selected from 250 mg/day, 500 mg/day, 750 mg/day, 1000 mg/day, 1250 mg/day, 1500 mg/day and 2000 mg/day.

9. A method according to claim 1, wherein the mammal is a human.

* * * * *